(12) United States Patent
Eshhar et al.

(10) Patent No.: US 8,211,422 B2
(45) Date of Patent: *Jul. 3, 2012

(54) CHIMERIC RECEPTOR GENES AND CELLS TRANSFORMED THEREWITH

(75) Inventors: Zelig Eshhar, Rehovot (IL); Daniel Schindler, Rehovot (IL); Tova Waks, Petach Tikva (IL); Gideon Gross, Hevel KoraZim (IL); Steven A. Rosenberg, Potomac, MD (US); Patrick Hwu, Rockville, MD (US)

(73) Assignees: The United States of America, as represented by the Secretary, Department of Health and Human Services, Washington, DC (US); Yeda Research and Development Co., Ltd., Rehovot (IL)

( * ) Notice: Subject to any disclaimer, the term of this patent is extended or adjusted under 35 U.S.C. 154(b) by 786 days.

This patent is subject to a terminal disclaimer.

(21) Appl. No.: 08/547,263

(22) Filed: Oct. 24, 1995
(Under 37 CFR 1.47)

(65) Prior Publication Data

US 2002/0137697 A1    Sep. 26, 2002

Related U.S. Application Data

(63) Continuation-in-part of application No. 08/084,994, filed on Jul. 2, 1993, now Pat. No. 7,741,465.

(30) Foreign Application Priority Data

Mar. 18, 1992  (IL) .......................................... 101288
Jan. 31, 1993  (IL) .......................................... 104570
Mar. 18, 1993  (WO) ....................... PCT/US93/02506

(51) Int. Cl.
A61K 48/00         (2006.01)
(52) U.S. Cl. ................. 424/93.21; 424/93.71; 514/44 R
(58) Field of Classification Search .................... 514/44, 514/44 R; 435/320.1, 325, 69.1, 235, 455; 424/277.1, 184.1, 135.1, 93.2, 93.21, 93.71; 536/23.1, 23.5, 23.4
See application file for complete search history.

(56) References Cited

U.S. PATENT DOCUMENTS 5,171,665 A  * 12/1992 Hellstrom et al. ............ 435/7.23
5,185,254 A  *  2/1993 Linnenbach .................. 435/69.3
5,266,478 A    11/1993 Chang et al.
5,359,046 A    10/1994 Capon et al.
5,840,301 A  * 11/1998 Rockwell et al. ........... 424/143.1
5,906,936 A     5/1999 Eshhar et al.
5,912,172 A     6/1999 Eshhar et al.
6,319,494 B1   11/2001 Capon et al.
6,407,221 B1    6/2002 Capon et al.

FOREIGN PATENT DOCUMENTS

| EP | 0180878 A2 | 5/1986 |
|---|---|---|
| EP | 0300793 A1 | 1/1989 |
| EP | 0340793 A2 | 11/1989 |
| WO | WO 8601533 A1 | 3/1986 |
| WO | WO 8809344 A1 | 12/1988 |
| WO | WO9210591 | 6/1992 |
| WO | WO9215322 | 9/1992 |
| WO | WO 93/19163 | 9/1993 |

OTHER PUBLICATIONS

Anderson WF, Nature 392:25-30, 1998.*
Verma et al Nature 389:239-242, 1997.*
Touchette, Nat. Med 2:7-8, 1996.*
Kay et al, PNAS 94:12744-76, 1997.*
Fahraeus et al, J. Pathol. 187:138-146, 1999.*
Shu et al, JAMA 278(22):1972-81, 1997.*
Rosenberg, Immunity, 10:281-287, 1999.*
Yee et al, Curr. Opin. Imm. 9:702-708, 1997.*
Eynde et al, Curr. Opin. Imm. 9:684-993, 1997.*
Pardoll et al Curr. Opin. Imm. 10:588-594, 1998.*
Willemsen et al. (1994) Gene Therapy, vol. 1 (Suppl. 2), meeting abstract.*
Hwu et al. (1993) J. Exp. Med., vol. 178, 361-366.*
ATCC Product Description of NCI-N87 Cell Line, ATCC Online Catalog, downloaded Jun. 29, 2010.*
P. Hwu, et al., "Lysis of Ovarian Cancer Cells by Human Lymphocytes Redirected with a Chimeric Gene Composed of an Antibody Variable Region and the Fc Receptor y Chain", The Journal of Experimental Medicine, vol. 178, Jul. 1993 361-366.
Anderson et al., Proc. Natl. Acad. Sci., 87, 2274-2278 (1990).
Barsumian et al., Eur. J. Immunol., 11, 317-323 (1981).
Cassatella et al., J. Exp. Med., 169, 549-567 (1989).
Colcher et al., J. Nat. Cancer Inst., 82, 1191-1197 (1990).
Herlyn et al., J. Immunol. Methods, 73, 157-167 (1984).
Hwu et al., J. Immunology, 150, 4104-4115 (1993).
Jain, Natl. Cancer Inst., 81, 57-576 (1989).
Köhler et al., Eur. J. Immunol., 6, 511-519 (1976).
Küster et al., J. Biol. Chem., 265, 6448-6452 (1990).
Lanier et al., Nature, 342, 803-805 (1989).
Lin et al., Science, 249, 677-679 (1990).
Lowder et al., Cancer Surv., 4, 359-375 (1985).
Lustgarten et al., Eur. J. Immunol., 25, 2985-2991 (1995).
Mosmann, J. Immunol. Methods, 65, 55-63 (1983).
Ravetch et al., J. Exp. Med., 170, 481-497 (1989).
Rusconi et al., Nature, 314, 330-334 (1985).
Schöneich et al., J. Immunol., 148, 2181-2185 (1992).
Snapper et al., J. Immunol., 141, 489-498 (1988).
Treisman et al., Blood, 85, 139-145 (1995).
Waldmann, Science, 252, 1657-1662 (1991).
Wegener et al., Cell, 68, 83-95 (1992).
Weiss et al., J. Exp. Med., 160, 1284-1299 (1984).

(Continued)

Primary Examiner — Anne Marie S Wehbe
(74) Attorney, Agent, or Firm — Leydig, Voit & Mayer

(57) ABSTRACT

Chimeric receptor genes suitable for endowing lymphocytes with antibody-type specificity include a first gene segment encoding a single-chain Fv domain of a specific antibody and a second gene segment encoding all or part of the transmembrane and cytoplasmic domains, and optionally the extracellular domain, of an immune cell-triggering molecule. The chimeric receptor gene, when transfected to immune cells, expresses the antibody-recognition site and the immune cell-triggering moiety into one continuous chain. The transformed lymphocytes are useful in therapeutic treatment methods.

30 Claims, 26 Drawing Sheets

OTHER PUBLICATIONS

U.S. Appl. No. 08/084,994, filed Jul. 2, 1993, Eshhar et al.
Adam et al., *J. Virology*, 65(9), 4985-4990 (Sep. 1991).
Anasetti et al., *J. Exp. Med.*, 172, 191-1700 (Dec. 1990).
Aruffo et al., *Proc. Natl. Acad. Sci.*, 84, 8573-8577 (Dec. 1987).
Bach et al., *Department of Chemical Immunology*, 1-26 (1995).
Bacus et al., *Cancer Research* 52, 2580-2589 (May 1, 1992).
Baroja et al., *Cell Immunol.* 120(1), 205-217 (Apr. 15, 1989).
Bauer et al., *Proc. Natl. Acad. Sci.*, 88, 3842-3846 (May 1991).
Becker et al., *Cell*, 58, 911-921 (Sep. 1989).
Benhamou et al., *J. Biol. Chem.*, 268(31), 23318-23324 (Nov. 5, 1993).
Berke, *Immunology Today*, 12(11), 396-399 (1991).
Bird et al, *Tibtech* 9(4), 132-137 (1991).
Bird et al., *Science*, 242, 423-426 (1988).
Bolen, *Cell Growth & Differentiation*, 2, 409-414 (Aug. 1991).
Bowen et al., *J. Immunology*, 151(11), 5896-5906 (Dec. 1993).
Burkhardt et al., *Molecular and Cellular Biology*, 14(2), 1095-1103 (Feb. 1994).
Celis et al., *Eur. J. Immunology*, 22, 3127-3134 (1992).
Chan et al., *Immunology* 88, 9166-9170 (Oct. 1991).
Chan et al., *Cell*, 71, 649-662 (Nov. 1992).
Chen et al., *Cell*, 71, 1093-1102 (Dec. 1992).
Ciccone et al., *Immunology Letters*, 31, 99-104 (1992).
Cline, *Schweiz Med Wochenschr.*, 116(43), 1459-1464 (Oct. 25, 1986).
Couture et al., *Proc. Natl. Acad. Sci.*, 91, 5301-5305 (Jun. 1994).
Culver et al., *PNAS*, 88, 3155-3159 (Apr. 1991).
Denny et al., *Nature*, 320, 549-551 (Apr. 1986).
Eshhar et al., "Modifying the specificity of T-cells using chimeric Ig/TCR genes," 345-368.
Eshhar et al., *Department of Chemical Immunology*, 1-10 (1995).
Eshhar et al., *J. Cancer*, 62, 27-29 (1990).
Eshhar et al., *J. Cellular Biochemistry*, Supplement 14B, 1990, UCLA Symposia on Molecular & Cellular Biology, Abstracts, 19$^{th}$ Annual Meeting, 70 (Jan. 27-Feb. 8, 1990).
Eshhar et al., *J. Immunology*, 124(2), 775-780 (Feb. 1980).
Eshhar et al., *Proc. Natl. Acad. Sci.*, 90, 720-724 (Jan. 1993).
Gascoigne et al., *Pro. Natl. Acad. Sci.*, 84, 2936-2940 (1987).
Gauen et al., *Mol. and Cell. Biol.*, 14(6), 3729-3741 (Jun. 1994).
Germann et al., *Eur. J. Immunology*, 21, 1857-1861 (1991).
Goverman et al., *Cell*, 60, 929-939 (Mar. 1990).
Gross et al., *PNAS*, 86, 10024-10028 (1989).
Gross et al., *Transplantation Proceedings*, 21(1), 127-130 (Feb. 1989).
Gross et al., Development and study of chimeric immunoglobulin/T cell receptor molecules as functional receptors that endow T cells with antibody-type specificity, Ph.D., *Thesis presented to the Feinberg Graduate School, The Wiezmann Institute of Science*, Rehovot, Israel, 1-70 (1990).
Gross et al., *FASEB, Department of Chemical Immunology*, 6, 3370-3378 (Dec. 1992).
Harding et al., *Nature*, 356, 607-609 (Apr. 1992).
Hatakeyama et al., *J. Exp. Med.* 166, 362-375 (1987).
Huston et al., *Proc. Natl. Acad. Sci*, 85, 5879-5883 (Aug. 1988).
Hutchcroft et al., *Proc. Natl. Acad. Sci.*, 89, 9107-9111 (Oct. 1990).
Hutchcroft et al., *J. Biol. Chem.*, 267(12), 8613-8619 (Apr. 25, 1992).
Hwu et al., *Cancer Detection and Prevention*, 18(1), 43-50 (1994).
Hwu et al., *Cancer Research*, 55, 3369-3372 (Aug. 1, 1995).
Irving et al., *Cell*, 64, 891-901 (Mar. 1991).
Kasid et al., *Proc. Natl. Acad. Sci*, 87, 473-477 (Jan. 1990).
Kaufmann et al., *Proc. Natl. Acad. Sci.*, 78(4), 2502-2506 (Apr. 1981).
Kimball, *J. Introduction to Immunology* (1983).
Kolnus et al., *Cell*, 74, 171-183 (Jul. 16, 1993).
Kuwana et al., *Biochemical and Biophysical Research Communications*, 149(3), 960-968 (Dec. 1987).
Lanier, *J. Immunology*, 146(5), 1571-1576 (Mar. 1, 1991).
Laroche et al., *J. Biol. Chem.*, 266, 16343-16349 (1991).
Law et al., *J. Biol. Chem.*, 269(16), 12310-12319 (Apr. 22, 1994).
Letourneur et al, *PNAS*, 88, 8905-8909 (Oct. 1991).
Lichtenheld et al., *Nature*, 335, 448-451 (Sep. 29, 1988).
Liou et al., *J. Immunol.*, 143, 3967-3975 (1989).
Mule et al., *Science*, 225, 1487-1489 (Sep. 28, 1984).
Orlff et al., *Nature*, 347, 189-191 (Sep. 13, 1990).
Ortaldo et al., *J. Exp. Med.*, 164, 1193-1205 (Oct. 1986).
Perussia et al., *Curr. Opin., Immunol.*, 3, 49-55 (1991).
Ravetch et al., *Annu. Rev. Immunol.*, 9, 457-492 (1991).
Romeo et al., *Cell*, 68, 889-897 (Mar. 6, 1992).
Romeo et al., *Cell*, 64(5), 1037-1046 (Mar. 8, 1991).
Rosenberg et al., *Science*, 233(19), 1318-1321 (Sep. 19, 1986).
Rosenberg et al., *New England J. of Med.*, 323(9), 570-578 (Aug. 30, 1990).
Rosenberg, *Scientific American*, 62-69 (May 1990).
Rosenberg et al., *J. of Clin. Oncology*, 10(2), 180-199 (Feb. 1992).
Rudd et al., *Immunology Today*, 15(5), 225-234 (1994).
Sato et al., *Science*, 268(21), 411-415 (Apr. 1995).
Schwarzbaum et al., *Eur. J. Immunol.*, 19, 1015-1023 (1989).
Shindo et al., *Immunology*, 71, 63-69 (1990).
Slamon et al., *Science*, 177-182 (Jan. 9, 1987).
Stancovski et al., *PNAS*, 88, 8691-8695 (Oct. 1991).
Stancovski et al., *J. Immunology*, 151(11), 6577-6582 (Dec. 1, 1993).
Taniguchi et al., *J. Biol. Chem.*, 266(24), 15790-15796 1991).
Truneh, *Nature*, 313(24), 318-320 (Jan. 24, 1985).
Unkeless et al., *Ann. Rev. Immunol*, 6, 251-281 (1988).
Van De Vijver et al., *New England J. of Med.*, 319(19), 1239-1245 (Nov. 10, 1988).
Vivier et al., *J. Immunol.*, 147(12), 4263-4270 (Dec. 15, 1991).
Hall, *Science*, 261, 915-918 (Aug. 1993).
Walsh et al., *J. Immunol.*, 153, 2506-2512 (1994).
Weaver et al., *Immunology Today*, 11(2), 49-54 (1990).
Weiss et al., *Advances in Immunology*, 41, 1-38 (1987).
Weiss et al., *Cell*, 76, 263-274 (Jan. 28, 1994).
Weissman et al., *The EMBO Journal*, 8(12), 3651-3656 (1989).
Wirthmueller et al., *J. Exp. Med.*, 175, 1381-1390 (May 1992).
Yague et al., *Cell*, 42, 81-87 (Aug. 1985).

\* cited by examiner

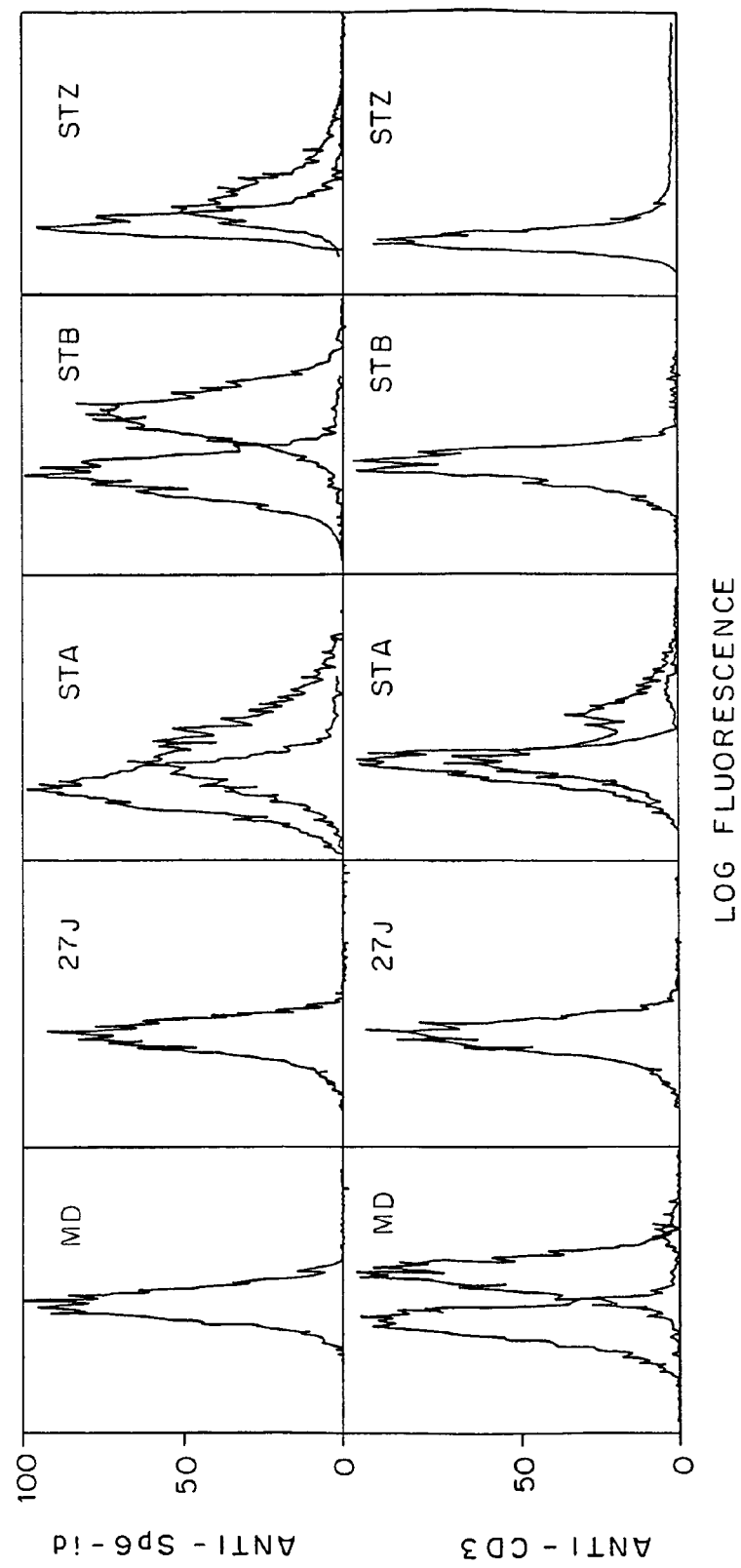

MD 27J STA STB   MD 27J STA STB

NON-REDUCED

MD 27J STA STB   MD 27J STA STB

REDUCED

ANTI-Sp6    ANTI-γ

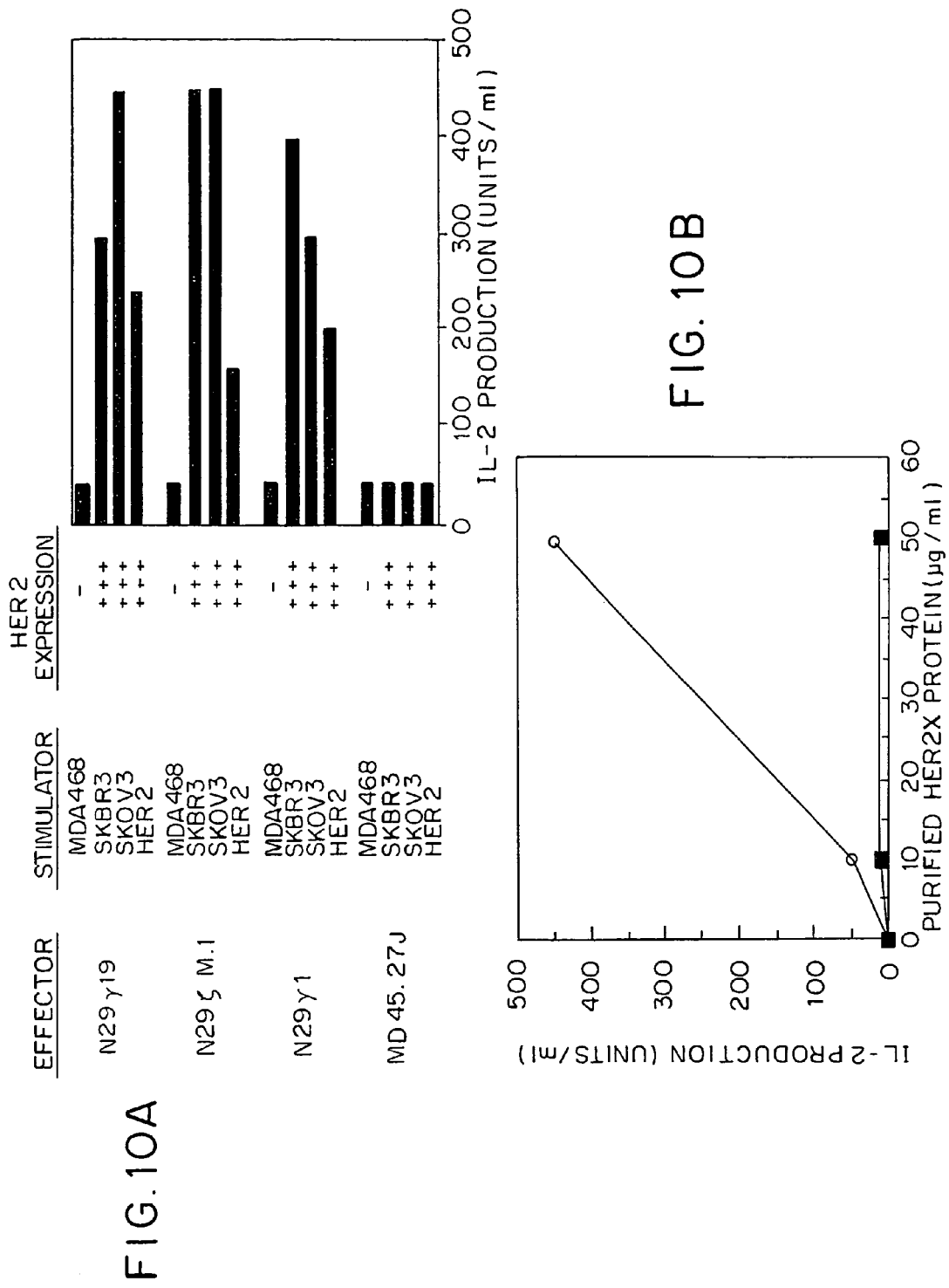

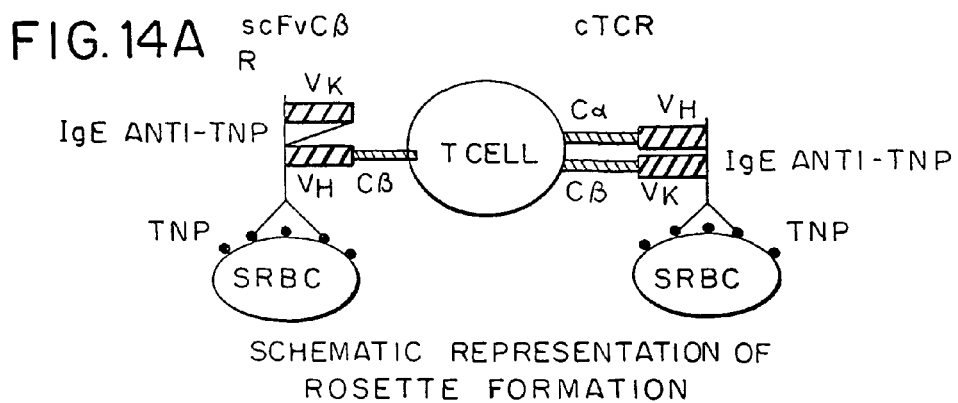
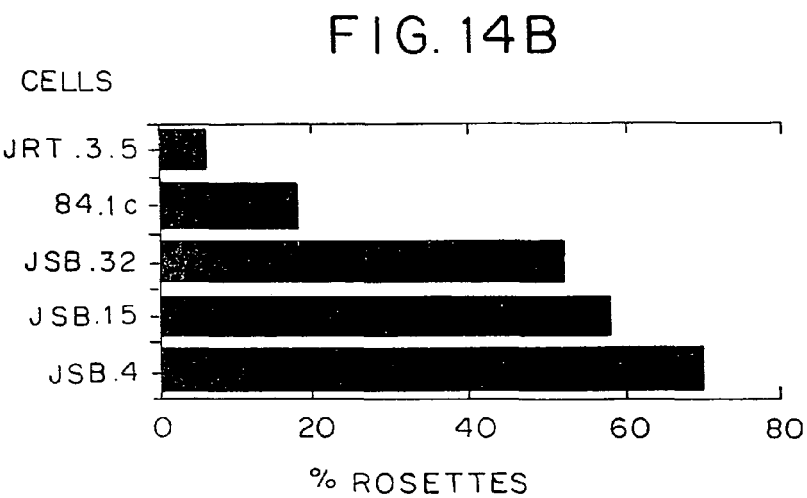
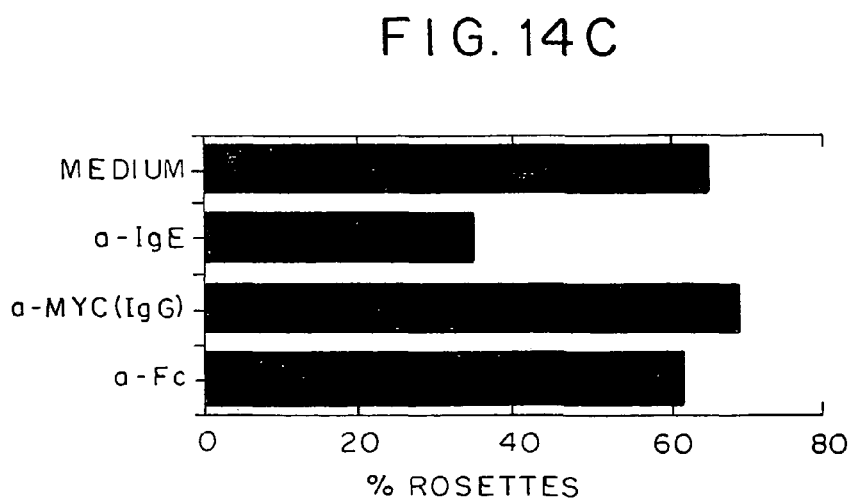

ELISA FOR SCREENING CELLS TRANSFECTED
WITH cTCR OR scFvR

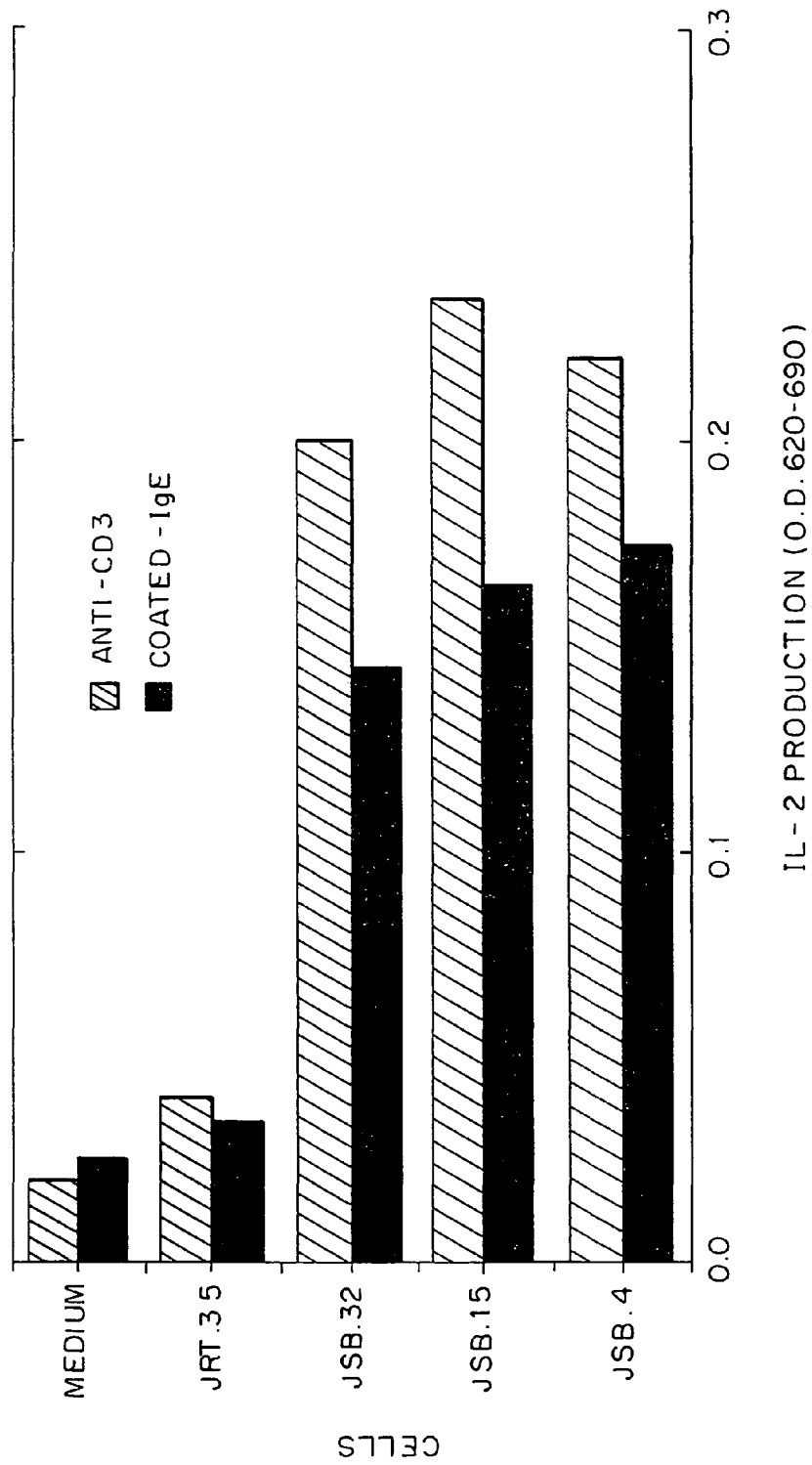

FIG. 18A

IgE SECRETION

- JSMB-4
- JSMB-9
- JSMB-17
- JSMB-28
- MD.45
- 84.1c
- MEDIUM

FIG. 18B

IgG SECRETION

- JSMB-4
- JSMB-9
- JSMB-17
- JSMB-28
- MD.45
- 84.1c
- MEDIUM

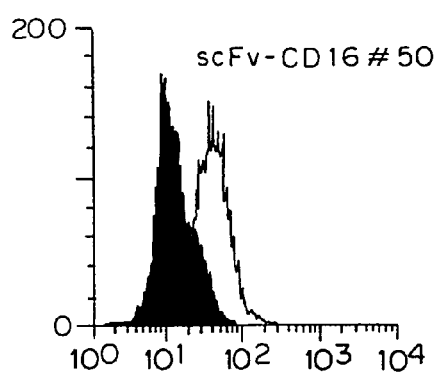 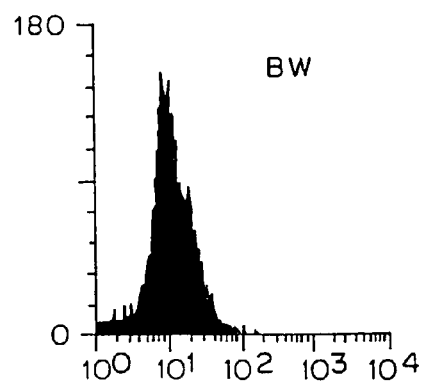
FIG. 22A  FIG. 22B
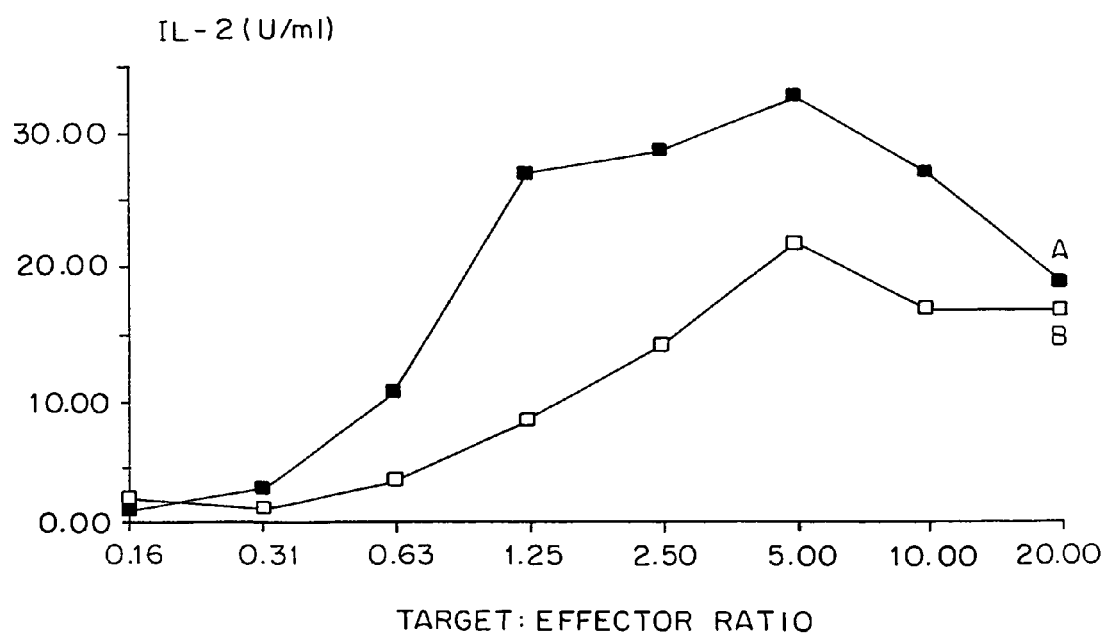
FIG. 23

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 15
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:1:

GGCCAGTGGA TAGAC                                                    15

(2) INFORMATION FOR SEQ ID NO:2:

(i) SEQUENCE CHARACTERISTICS:
        (A) LENGTH: 15
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:2:

GATGGTGGGA AGATG                                                    15

(2) INFORMATION FOR SEQ ID NO:3:

(i) SEQUENCE CHARACTERISTICS:
        (A) LENGTH: 19
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:3:

CCATGRYGTA TACCTGTGG                                                19

(2) INFORMATION FOR SEQ ID NO:4:

(i) SEQUENCE CHARACTERISTICS:
        (A) LENGTH: 37
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:4:

CCCGTCTAGA GGAGAYATYG TWATGACCCA GTCTCCA                             37

(2) INFORMATION FOR SEQ ID NO:5:

(i) SEQUENCE CHARACTERISTICS:
        (A) LENGTH: 32
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:5:

CCCGTCGACC CTTTWATTTC CAGCTTWGTS CC                          32

(2) INFORMATION FOR SEQ ID NO:6:

(i) SEQUENCE CHARACTERISTICS:
        (A) LENGTH: 47
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:6:

CGGGTCGACT TCCGGTAGCG GCAAATCCTC TGAAGGCAAA                  40

GGTSAGG                                                     47

(2) INFORMATION FOR SEQ ID NO:7:

(i) SEQUENCE CHARACTERISTICS:
        (A) LENGTH: 34
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:7:

TGMRGAGACG GTGACCGTRG TYCCTTGGCC CCAG                        34

(2) INFORMATION FOR SEQ ID NO:8:

(i) SEQUENCE CHARACTERISTICS:
        (A) LENGTH: 37
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:8:

CCTCGAGATA AAAATATCC AGAACCCTGA CCCTGCC                      37

(2) INFORMATION FOR SEQ ID NO:9:

(i) SEQUENCE CHARACTERISTICS:
        (A) LENGTH: 41
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:9:

CGGTCACCGT CTCCTCAAAT ATCCAGAACC CTGACCCTGC                  40

C                                                           41

(2) INFORMATION FOR SEQ ID NO:10:

(i) SEQUENCE CHARACTERISTICS:
        (A) LENGTH: 37
        (B) TYPE: NUCLEOTIDE
        (C) STRANDEDNESS: DOUBLE
        (D) TOPOLOGY: UNKNOWN (xi) SEQUENCE DESCRIPTION:SEQ ID NO:10:

CCTCGAGATA AAAGAGGACC TGAAAAACGT GTTCCCA                     37

(2) INFORMATION FOR SEQ ID NO:11:

(i) SEQUENCE CHARACTERISTICS:
        (A) LENGTH: 41
        (B) TYPE: NUCLEOTIDE
        (C) STRANDEDNESS: DOUBLE (D) TOPOLOGY: UNKNOWN (xi) SEQUENCE DESCRIPTION:SEQ ID NO:11:

CGGTCACCGT CTCCTCAGAG GACCTGAAAA ACGTGTTCCC                40

A                                                         41

(2) INFORMATION FOR SEQ ID NO:12:

(i) SEQUENCE CHARACTERISTICS:
            (A) LENGTH: 33
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:12:

TACGTATCAG CTGGACCACA GCCGCAGCGT CAT                       33

(2) INFORMATION FOR SEQ ID NO:13:

(i) SEQUENCE CHARACTERISTICS:
            (A) LENGTH: 33
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:13:

TACGTATCAG CCTCTGGAAT CCTTTCTCTT GAC                       33

(2) INFORMATION FOR SEQ ID NO:14:

(i) SEQUENCE CHARACTERISTICS:
            (A) LENGTH: 47
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:14:

CCGGTCACCG TCTCTTCAGC GGATCCTCAG CTCTGCTATA TCCTGGA        47

(2) INFORMATION FOR SEQ ID NO:15:

(i) SEQUENCE CHARACTERISTICS:
            (A) LENGTH: 33
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:15:

GGCAGCTGCT CGAGTCTAAA GCTACTGTGG TGG                       33

(2) INFORMATION FOR SEQ ID NO:16:

(i) SEQUENCE CHARACTERISTICS:
            (A) LENGTH: 23
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:16:

GCTGGATCCC AAACTCTGCT ACC                                  23

(2) INFORMATION FOR SEQ ID NO:17:

(i) SEQUENCE CHARACTERISTICS:
            (A) LENGTH: 25
            (B) TYPE: NUCLEOTIDE
            (C) STRANDEDNESS: DOUBLE (D) TOPOLOGY: UNKNOWN (xi) SEQUENCE DESCRIPTION:SEQ ID NO:17:

CGCCTCGAGC TGTTAGCGAG GGGGC                                         25

(2) INFORMATION FOR SEQ ID NO:18:

(i) SEQUENCE CHARACTERISTICS:
            (A) LENGTH: 39
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:18:

CCGGTCACCG TCTCCTCAGG GTACCAAGTC TCTTTCTGC                           39

(2) INFORMATION FOR SEQ ID NO:19:

(i) SEQUENCE CHARACTERISTICS:
            (A) LENGTH: 26
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:19:

CCCTCGAGTC ATTTGTCTTG AGGGTC                                        26

(2) INFORMATION FOR SEQ ID NO:20:

(i) SEQUENCE CHARACTERISTICS:
            (A) LENGTH: 47
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:20:

CCGGTCACCG TCTCTTCAGC GGATCCTACC ATTCCGTGGC TCGGCCA                  47

(2) INFORMATION FOR SEQ ID NO:21:

(i) SEQUENCE CHARACTERISTICS:
            (A) LENGTH: 20
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:21:

GGAGATAGAA GCTTGCCAGG                                               20

(2) INFORMATION FOR SEQ ID NO:22:

(i) SEQUENCE CHARACTERISTICS:
            (A) LENGTH: 20
            (B) TYPE: NUCLEOTIDE
            (C) STRANDEDNESS: DOUBLE
            (D) TOPOLOGY: UNKNOWN (xi) SEQUENCE DESCRIPTION:SEQ ID NO:22:

CCTGGCAAGC TTCTATCTCC                                               20

(2) INFORMATION FOR SEQ ID NO:23:

(i) SEQUENCE CHARACTERISTICS:
            (A) LENGTH: 28
            (B) TYPE: NUCLEOTIDE
            (C) STRANDEDNESS: DOUBLE
            (D) TOPOLOGY: UNKNOWN

```
(xi) SEQUENCE DESCRIPTION:SEQ ID NO:23:

GGCTCGAGTC TACACCAAGT GAGTTGGG                                              28
```

CHIMERIC RECEPTOR GENES AND CELLS TRANSFORMED THEREWITH

This application is a continuation in part of U.S. application Ser. No. 08/084,994 filed Jul. 2, 1993 now U.S. Pat. No. 7,741,465 which is herein incorporated by reference in toto.

FIELD OF THE INVENTION

The present invention relates to chimeric receptor genes suitable for endowing lymphocytes with antibody-type specificity, to expression vectors comprising said chimeric genes and to lymphocytes transformed with said expression vectors. Various types of lymphocyte cells are suitable, for example, cytotoxic T cells, helper T cells, natural killer (NK) cells, etc. The transformed lymphocytes are useful in therapeutic treatment methods.

BACKGROUND OF THE INVENTION

Cells of the immune system are known to recognize and interact with specific molecules by means of receptors or receptor complexes which, upon recognition or an interaction with such molecules, causes activation of the cell to perform various functions. An example of such a receptor is the antigen-specific T cell receptor complex (TCR/CD3).

The T cell receptor for antigen (TCR) is responsible for the recognition of antigen associated with the major histocompatibility complex (MHC). The TCR expressed on the surface of T cells is associated with an invariant structure, CD3. CD3 is assumed to be responsible for intracellular signalling following occupancy of the TCR by ligand.

The T cell receptor for antigen-CD3 complex (TCR/CD3) recognizes antigenic peptides that are presented to it by the proteins of the major histocompatibility complex (MHC). Complexes of MHC and peptide are expressed on the surface of antigen presenting cells and other T cell targets. Stimulation of the TCR/CD3 complex results in activation of the T cell and a consequent antigen-specific immune response. The TCR/CD3 complex plays a central role in the effector function and regulation of the immune system.

Two forms of T cell receptor for antigen are expressed on the surface of T cells. These contain either α/β heterodimers or γ/δ heterodimers. T cells are capable of rearranging the genes that encode the α, β, γ and δ chains of the T cell receptor. T cell receptor gene rearrangements are analogous to those that produce functional immunoglobulins in B cells and the presence of multiple variable and joining regions in the genome allows the generation of T cell receptors with a diverse range of binding specificities. Each α/β or γ/δ heterodimer is expressed on the surface of the T cell in association with four invariant peptides. These are the γ, E and ε subunits of the CD3 complex and the zeta chain. The CD3 γ, δ and ε polypeptides are encoded by three members of the immunoglobulin supergene family and are found in a cluster on human chromosome 11 or murine chromosome 9. The zeta chain gene is found separately from other TCR and CD3 genes on chromosome 1 in both the mouse and human. Murine T cells are able to generate a receptor-associated η chain through alternative splicing of the zeta m-RNA transcript. The CD3 chains and the zeta subunit do not show variability, and are not involved directly in antigen recognition.

All the components of the T cell receptor are membrane proteins and consist of a leader sequence, externally-disposed N-terminal extracellular domains, a single membrane-spanning domain, and cytoplasmic tails. The α, β, γ and δ antigen-binding polypeptides are glycoproteins. The zeta chain has a relatively short ectodomain of only nine amino acids and a long cytoplasmic tail of approximately 110 amino acids. Most T cell receptor α/β heterodimers are covalently linked through disulphide bonds, but many γ δ receptors associate with one another non-covalently. The zeta chain quantitatively forms either disulphide-linked ζ-η heterodimers or zeta-zeta homodimers.

Another example of a type of receptor on cells of the immune system is the Fc receptor. The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation, phagocytosis and target cell lysis. All these interactions are initiated through the binding of the Fc domain of antibodies or immune complexes to specialized cell surface receptors on hematopoietic cells. It is now well established that the diversity of cellular responses triggered by antibodies and immune complexes results from the structural heterogeneity of Fc receptors (FcRs).

FcRs are defined by their specificity for immunoglobulin isotypes. Fc receptors for IgG are referred to as FcγR, for IgE as FcεR, for IgA as FcαR, etc. Structurally distinct receptors are distinguished by a Roman numeral, based on historical precedent. We now recognize three groups of FcγRs, designated FcγRI, FcγRII, and FcγRIII. Two groups of FcεR have been defined; these are referred to as FcεRI and FcεRII. Structurally related although distinct genes within a group are denoted by A, B, C. Finally, the protein subunit is given a Greek letter, such as FcγRIIIAα, FcγRIIIAγ.

Considerable progress has been made in the last three years in defining the heterogeneity for IgG and IgE Fc receptors (FcγR, FcεR) through their molecular cloning. Those studies make it apparent that Fc receptors share structurally related ligand binding domains, but differ in their transmembrane and intracellular domains which presumably mediate intracellular signalling. Thus, specific FcγRs on different cells mediate different cellular responses upon interaction with an immune complex. The structural analysis of the FcγRs and FcεRI has also revealed at least one common subunit among some of these receptors. This common subunit is the γ subunit, which is similar to the ζ or η chain of the TCR/CD3, and is involved in the signal transduction of the FcγRIII and FcεRI.

The low affinity receptor for IgG (FcγRIIIA), is composed of the ligand binding CD16α (FcγRIIIAα) polypeptide associated with the γ chain (FcγRIIIAγ). The CD16 polypeptide appears as membrane anchored form in polymorphonuclear cells and as transmembrane form ($CD16_{TM}$) in NK. The FcγRIIIA serves as a triggering molecule for NK cells.

Another type of immune cell receptor is the IL-2 receptor. This receptor is composed of three chains, the α chain (p55), the β chain (p75) and the γ chain. When stimulated by IL-2, lymphocytes undergo proliferation and activation.

Antigen-specific effector lymphocytes, such as tumor specific T cells (Tc), are very rare, individual-specific, limited in their recognition spectrum and difficult to obtain against most malignancies. Antibodies, on the other hand, are readily obtainable, more easily derived, have wider spectrum and are not individual-specific. The major problem of applying specific antibodies for cancer immunotherapy lies in the inability of sufficient amounts of monoclonal antibodies (mAb) to reach large areas within solid tumors. In practice, many clinical attempts to recruit the humoral or cellular arms of the immune system for passive anti-tumor immunotherapy have not fulfilled expectations. While it has been possible to obtain anti-tumor antibodies, their therapeutic use has been limited so far to blood-borne tumors (1, 2) primarily because solid tumors are inaccessible to sufficient amounts of antibodies (3). The use of effector lymphocytes in adoptive immunotherapy, although effective in selected solid tumors, suffers on the other hand, from a lack of specificity (such as in the case of lymphokine-activated killer cells (LAK cells) (4) which are mainly NK cells) or from the difficulty in recruiting tumor-infiltrating lymphocytes (TILs) and expanding such specific T cells for most malignancies (5). Yet, the observations that TILs can be obtained in melanoma and renal cell carcinoma tumors, that they can be effective in selected patients and that foreign genes can function in these cells (6) demonstrate the therapeutic potential embodied in these cells.

A strategy which has been recently developed (European Published Patent Application No. 0340793, Ref. 7-11) allows one to combine the advantage of the antibody's specificity with the homing, tissue penetration, cytokine production and target-cell destruction of T lymphocytes and to extend, by ex vivo genetic manipulations, the spectrum of anti-tumor specificity of T cells. In this approach the laboratory of the present inventors succeeded to functionally express in T cells chimeric T cell receptor (cTCR) genes composed of the variable region domain (Fv) of an antibody molecule and the constant region domain of the antigen-binding TCR chains, i.e., the $\alpha/\beta$ or $\gamma/\delta$ chains. In this gene-pairs approach, genomic expression vectors have been constructed containing the rearranged gene segments coding for the V region domains of the heavy ($V_H$) and light ($V_L$) chains of an anti-2,4,6-trinitrophenyl (TNP) antibody (Sp6) spliced to either one of the C-region gene segments of the $\alpha$ or $\beta$ TCR chains. Following transfection into a cytotoxic T-cell hybridoma, expression of a functional TCR was detected. The chimeric TCR exhibited the idiotope of the Sp6 anti-TNP antibody and endowed the T cells with a major histocompatibility complex (MHC) nonrestricted response to the hapten TNP. The transfectants specifically killed TNP-bearing target cells, and produced interleukin-2 (IL-2) in response thereto across strain and species barriers. Moreover, such transfectants responded to immobilized TNP-protein conjugates, bypassing the need for cellular processing and presentation. The chimeric TCRs could provide T cells with an antibody-like specificity and, upon encountering antigen, were able to effectively transmit signals for T cell activation, secretion of lymphokines and specific target cell lysis in a MHC nonrestricted manner. Moreover, the cTCR bearing cells undergo stimulation by immobilized antigen, proving that receptor-mediated T-cell activation is not only nonrestricted but also independent of MHC expression on target cells (8, 9). New expression cassettes were also developed based on reverse transcription of mRNA and PCR amplification of rearranged $V_H$ and $V_L$ DNA, using primers based on 3' and 5' consensus sequences (12) of these genes which allow rapid construction of cTCR genes from any mAb-producing hybridoma. To determine the therapeutic potential of the chimeric TCR approach, we successfully constructed and functionally expressed cTCR genes composed of combining sites of anti-idiotypic antibody specific to the surface IgM of the 38C13 murine B lymphoma cell line.

Broad application of the cTCR approach is dependent on efficient expression of the cTCR genes in primary T cells. So far, utilizing protoplast fusion, lipofection or electroporation, we succeeded in expressing the cTCR in T cell hybridomas (8, 9) or human T cell tumors, such as Jurkat, but like others, achieved only limited and transient expression in non-transformed murine T cell lines. Although retroviral vectors have been demonstrated to be effective for transgene expression in human T cells (13, 14), due to the fact that two genes have to be introduced in order to express functional cTCR; ($C\alpha V_H$+$C\beta V_L$ or $C\alpha V_L$+$C\beta V_H$), and the very low efficiency of transduction of a single cell with two separate retroviral vectors, new vectors have to be tried which will allow the transduction of two genes in tandem (15).

Another strategy which has recently been developed employs joining of the extracellular ligand binding domain of receptors such as CD4, CD8, the IL-2 receptor, or CD16, to the cytoplasmic tail of either one of the $\gamma/\zeta$ family members (26-28, 38). It has been shown that crosslinking of such extracellular domains through a ligand or antibody results in T cell activation. Chimeric CD4 or CD16-$\gamma/\zeta$ molecules expressed in cytotoxic lymphocytes could direct specific cytolysis against appropriate target cells (26, 38). In PCT WO92/15322 it is suggested that the formation of chimeras consisting of the intracellular portion of T cell/Fc receptor $\zeta$, $\epsilon$ or $\gamma$ chains joined to the extracellular portion of a suitably engineered antibody molecule will allow the target recognition potential of an immune system cell to be specifically redirected to the antigen recognized by the extracellular antibody portion. However, while specific examples are present showing that such activation is possible when the extracellular portion of receptors such as the CD4 receptor are joined to such $\zeta$, $\eta$ or $\gamma$ chains, no proof was presented that when a portion of an antibody is joined to such chains one can obtain expression in lymphocytes or activation of lymphocytes.

SUMMARY OF THE INVENTION

It has now been found according to the present invention that by fusing a single-chain Fv domain (scFv) gene of a specific antibody, composed of $V_L$ linked to $V_H$ by a flexible linker, with a gene segment encoding a short extracellular and the entire transmembrane and cytoplasmic domains of a lymphocyte-activation molecule, a chimeric gene is obtained which combines the antibody recognition site and the lymphocyte-signalling moiety into one continuous chain. Upon transfection of such chimeric scFv-receptor (c-scFvR) gene into lymphocytes, it is expressed in the cell as a functional receptor and endows the cells with antibody-type specificity.

The present invention thus relates to chimeric genes suitable to endow lymphocyte cells with antibody-type specificity. Various types of lymphocytes are suitable, for example, natural killer cells, helper T cells, suppressor T cells, cytotoxic T cells, lymphokine activated cells, subtypes thereof and any other cell type which can express chimeric receptor chain.

The chimeric gene comprises a first gene segment encoding the scFv of a specific antibody, i.e., DNA sequences encoding the variable regions of the heavy and light chains ($V_H$ and $V_L$, respectively) of the specific antibody, linked by a flexible linker, and a second gene segment which comprises a DNA sequence encoding partially or entirely the transmembrane and cytoplasmic, and optionally the extracellular, domains of a lymphocyte-triggering molecule corresponding to a lymphocyte receptor or part thereof.

The present invention further relates to suitable vectors for transfecting cells of the type defined above with the chimeric gene.

The present invention further relates to cells of the type defined above into which such chimeric gene has been introduced so as to obtain its expression, and also to pharmaceutical prophylactic and curative compositions containing an effective quantity of such cells.

In general terms, the present invention relates to a process for the generation of lymphocytes transfected with an expression vector containing a chimeric gene of the invention. As set out in the following, there was constructed a model system which comprises an expression vector which was transfected into cytotoxic T cells and which was functionally expressed in said cells, i.e., which directed the cellular response of the lymphocyte against a predefined target antigen in a MHC nonrestricted manner.

The genetically engineered lymphocyte cells of the present invention may be used in new therapeutic treatment processes. For example, T cells or NK cells isolated from a patient may be transfected with DNA encoding a chimeric gene including the variable region of an antibody directed toward a specific antigen, and then returned to the patient so that the cellular response generated by such cells will be triggered by and directed toward the specific antigen in a MHC nonrestricted manner. In another embodiment, peripheral blood cells of the patient are genetically engineered according to the invention and then administered to the patient.

Because of the restrictions imposed by corecognition of self MHC plus antigen, the acquisition of new specificity by grafting of TCR genes is limited to inbred combinations. Such manipulations are practically impossible in an outbred population. However, the present invention allows us to confer antibody specificity using not only the TCR components, but other lymphocyte-signalling chains, such as the zeta/eta chains of CD3, $\gamma$ chain of the Fc$\gamma$R and Fc$\epsilon$R, $\alpha$, $\beta$ and $\gamma\psi$ chains of the IL-2R or any other lymphokine receptor, CD16 $\alpha$-chain, CD2, CD28, and others. Thus, grafting the chimeric genes into NK cells which are not antigen-specific will endow them with antibody specificity.

These primers were designed to match the consensus sequences of $V_H$ and $V_L$. The relevant restriction sites are in bold letters.

FIG. 3 shows the fluorescence-activated cell sorter (FACS) analysis of immunofluorescence staining of MD.45 hybridoma and its TCR $\alpha$-MD45.27J mutant, their corresponding scFvR$\gamma$-transfected STA and STB clones, or STZ cells, which result from transfection of the scFvR$\zeta$ chimeric gene into MD45.27J. Solid line, staining with anti-Sp6 idiotypic antibody 20.5 or anti-CD3 mAb 145.2Cll. Broken line represents control irrelevant antibody.

Figures 4A, 4B:
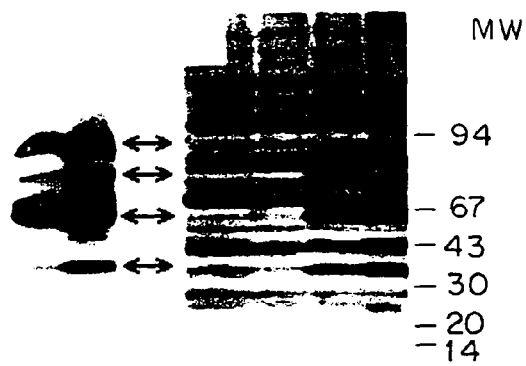
Figures 4C, 4D:

FIGS. 4A-4D show immunoblotting analysis of lysates prepared from scFvR$\gamma$ transfectants and parental hybridomas developed by anti-Sp6 idiotypic mAb 20.5 (FIGS. 4A and 4C, respectively) and rabbit anti-human gamma chain (FIGS. 4B and 4D, respectively). Electrophoresis was on four separate gels. The molecular mass scales are related to B and D; the arrows point to the same bands in A and B or C and D.

Figure 5A:
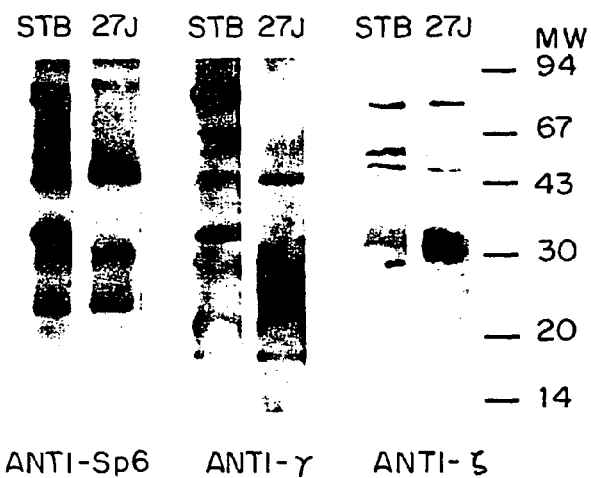
Figure 5B:
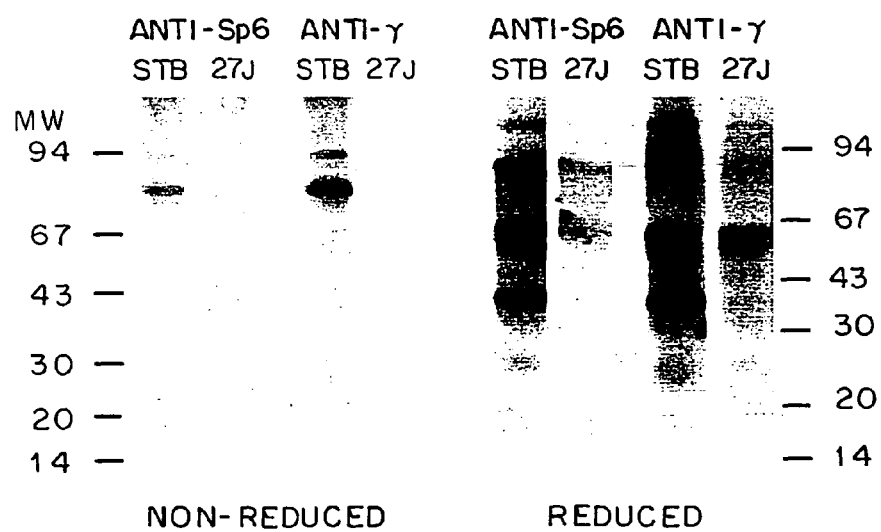

FIGS. 5A and 5B show the composition of the scFvR$\gamma$ dimers. FIG. 5A—Immunoblot analysis of anti-Sp6 precipitates prepared from STB (scFvR$\gamma$ transfectant cells), and their parent (MD45.27J hybridoma cells). After electrophoresis under non-reducing conditions and blotting, the blot was allowed to react with anti-Sp6, anti-human gamma, or anti-mouse $\zeta$ antibodies. FIG. 5B—Immunoprecipitation of lysates made of surface-iodinated STB cells (scFvR$\gamma$ transfectant cells) and their parent (MD45.27J hybridoma cells).

Figure 6A:
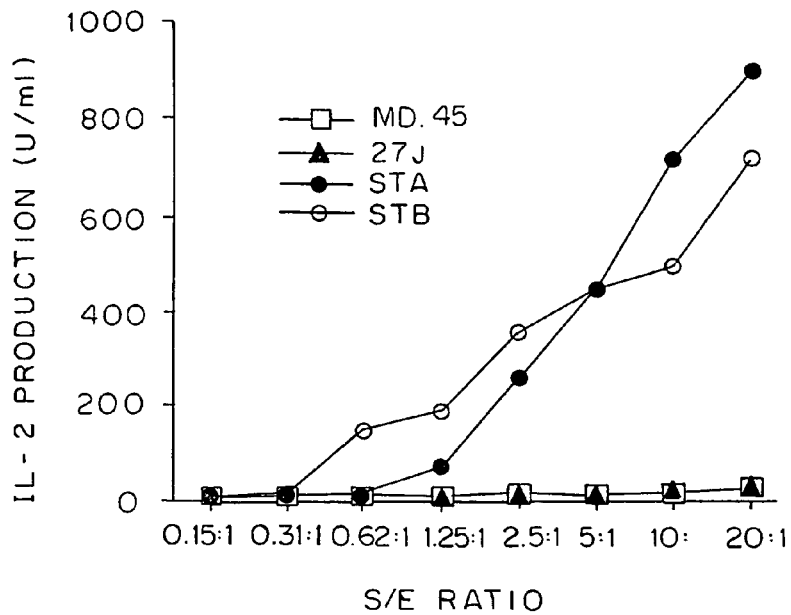
Figure 6B:
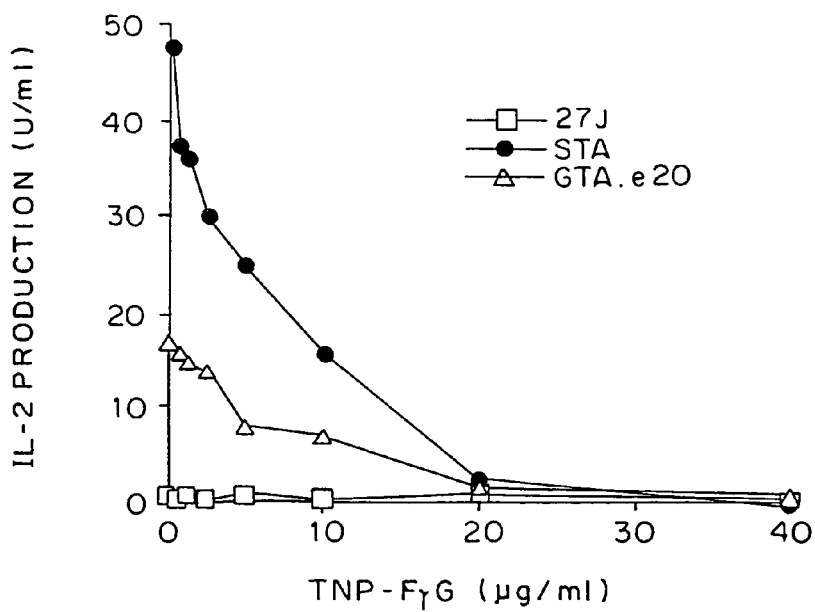

FIGS. 6A-6B illustrates that transfectants expressing scFvR are stimulated to produce IL-2 after stimulation with TNP-A.20 (FIG. 6A), or plastic immobilized TNP-F$\gamma$G, without or with different concentrations of soluble TNP-F$\gamma$G (FIG. 6B). GTAc.20 is an SpG double-chain cTCR transfectant described previously (9). The scFvR zeta-expressing STZ produced about 200 units (U) of IL-2 per ml after co-culture with TNP-A.20 at 8:1 stimulator-to-effector (S/E) cell ratio. Not shown are the responses of the transfectants to non-modified A.20 or F$\gamma$G controls, which were completely negative, exactly like the background responses of the MD.45 and MD45.27J to TNP antigen.

Figure 7A:
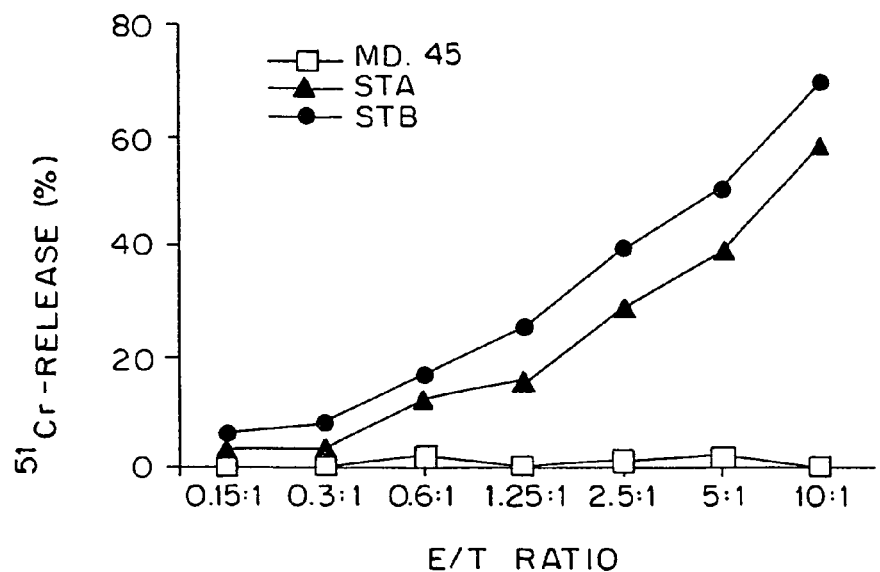
Figure 7B:
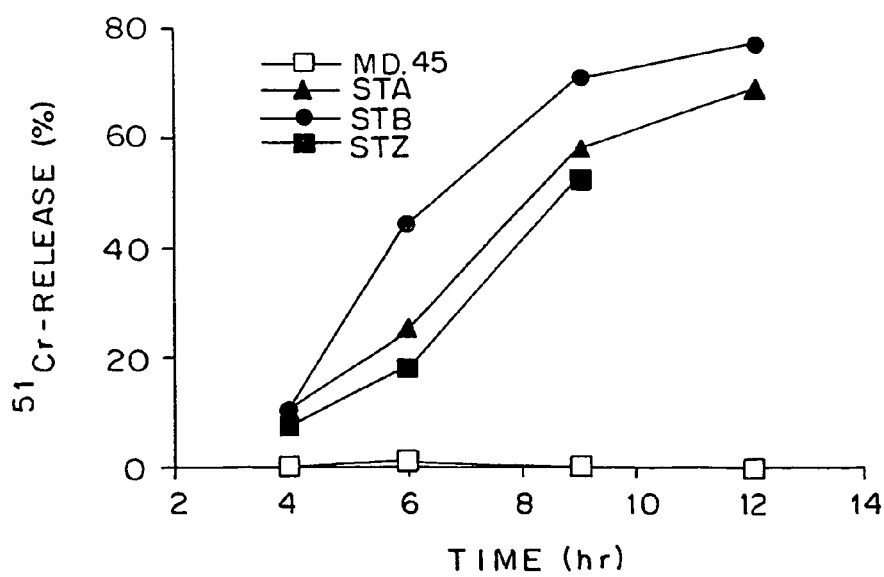
Figure 8B:
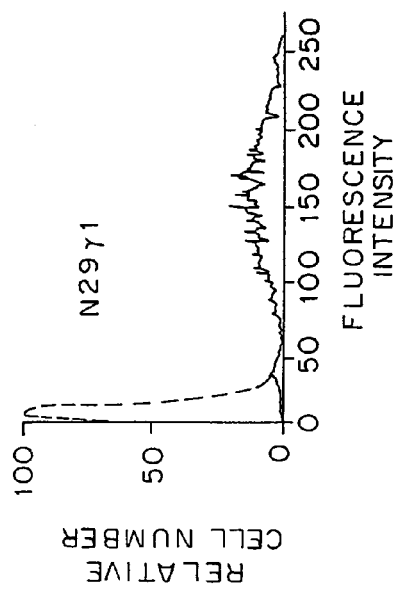
Figure 8D:
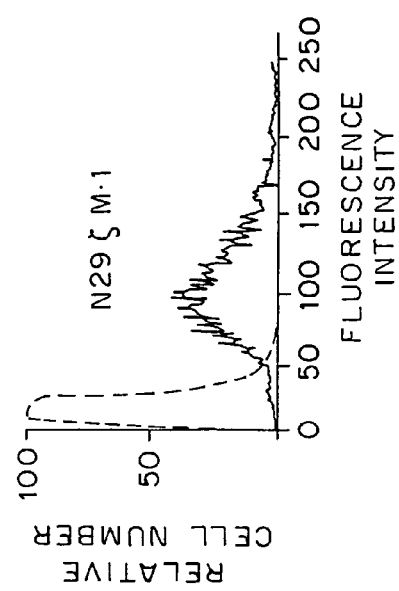
Figure 8A:
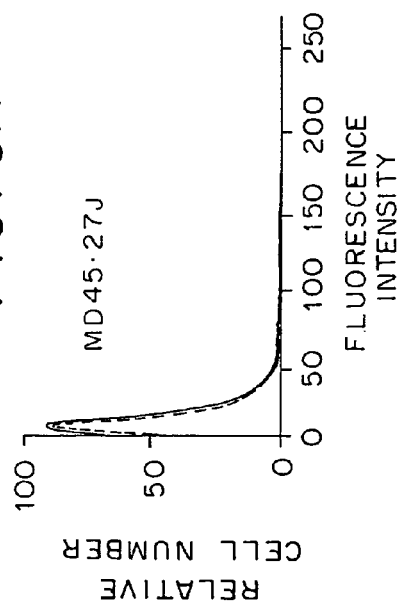
Figure 8C:
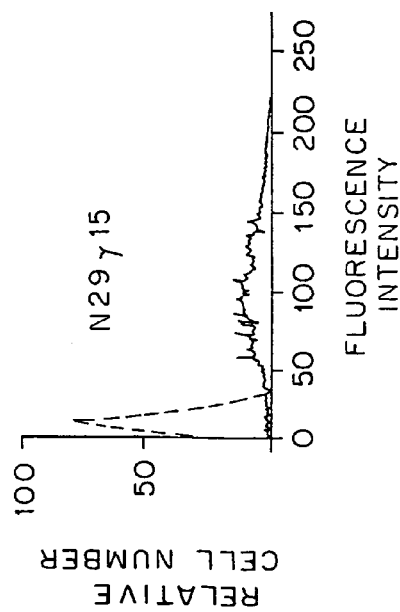

FIGS. 7A and 7B show specific $^{51}$Cr release of TNP-A.20 cells after incubation with transfectants expressing scFvR. Effector cells were incubated with plastic-immobilized TNP-F$\gamma$G for 8 hr before the killing assay. Kinetic assay was done at an effector-to-target (E/T) cell ratio of 10:1 (FIG. 7A); dose response was determined in a 9 hr assay (FIG. 7B). Control non-modified A.20 target cells incubated with the same effector cells in identical conditions did not release more $^{51}$Cr than the spontaneous release (not shown).

FIGS. 8A-8D show surface expression of chimeric scFvR$\gamma$/$\zeta$. T cell hybridoma transfected with the scFvR$\gamma$ (N29$\gamma$1, N29$\gamma$15) or scFvR$\zeta$ (N29$\zeta$M.1) chimeric genes composed of the variable region of N29 anti-HER2 mAb, were stained with anti-N29 idiotypic antibodies or control serum (broken lines) and analyzed by FACS.

Figure 9A:
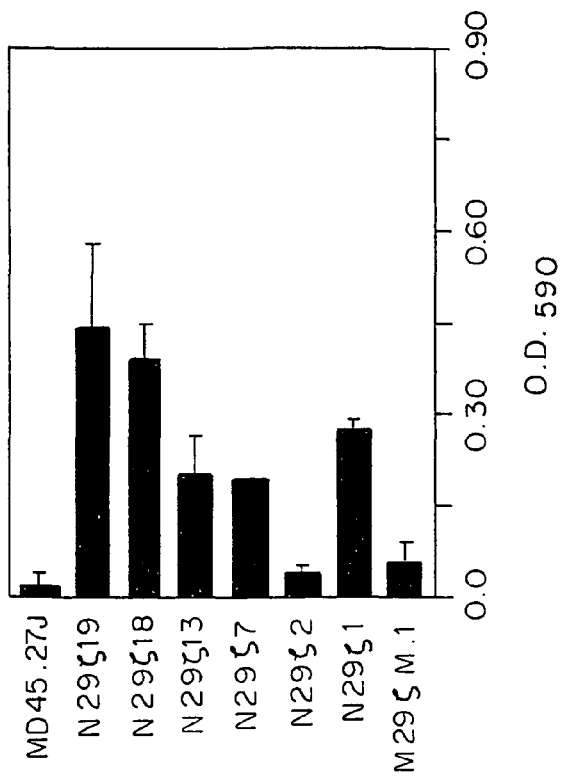
Figure 9B:
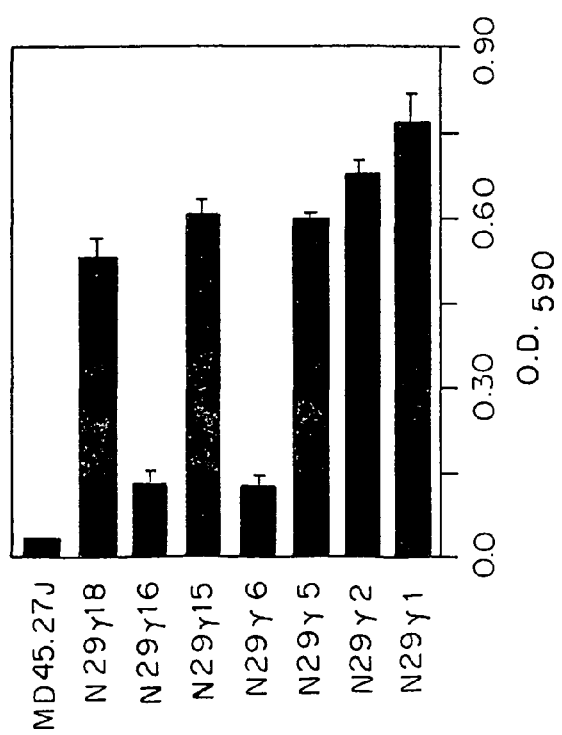

FIGS. 9A and 9B show binding of detergent-solubilized scFvN29R$\gamma$ and scFvN29R$\zeta$ to Neu/HER2 antigen. The presence of chimeric receptors in cell lysates was evaluated by ELISA using HER2X-coated wells and anti-$\gamma$ (FIG. 9A) or anti-$\zeta$ (FIG. 9B) antibodies. Functional molecules derived from hybridomas expressing the chimeric transgenes could bind to the immobilized antigen and expressed antigenic determinants specific to either $\gamma$ or $\zeta$ polypeptides.

FIGS. 10A and 10B shows antigen-specific activation of chimeric receptor expressing cells by HER2-bearing stimulator cells (FIG. 10A) or immobilized HER2X protein (FIG. 10B). T cell hybridomas expressing the chimeric scFvN29R$\gamma$/$\zeta$ genes underwent antigen-specific, but MHC unrestricted stimulation for IL-2 production following co-culture with either HER2-expressing cells of different origins or with plastic-bound purified HER2/Neu receptor. Stimulator cells used were human breast carcinoma cell lines SKBR3 and MDA 468, the human ovarian carcinoma cell line SKOV3 or HER2, a c-erbB-2 transfected 3T3-NIH fibroblasts (kindly provided by Dr. A. Ullrich). The Neu/HER2 protein is overexpressed in SKBR3, SKOV3 and HER2, while the MDA 468 cells have undetectable surface receptor. As shown, untransfected parental cells MD45.27J did not produce any IL-2 following incubation with Neu/HER2 expressing cells. In B, [filled square]—MD45.27J, untransfected cells; O—N29γ1, transfectant expressing scFvN29Rγ.

Figure 11:
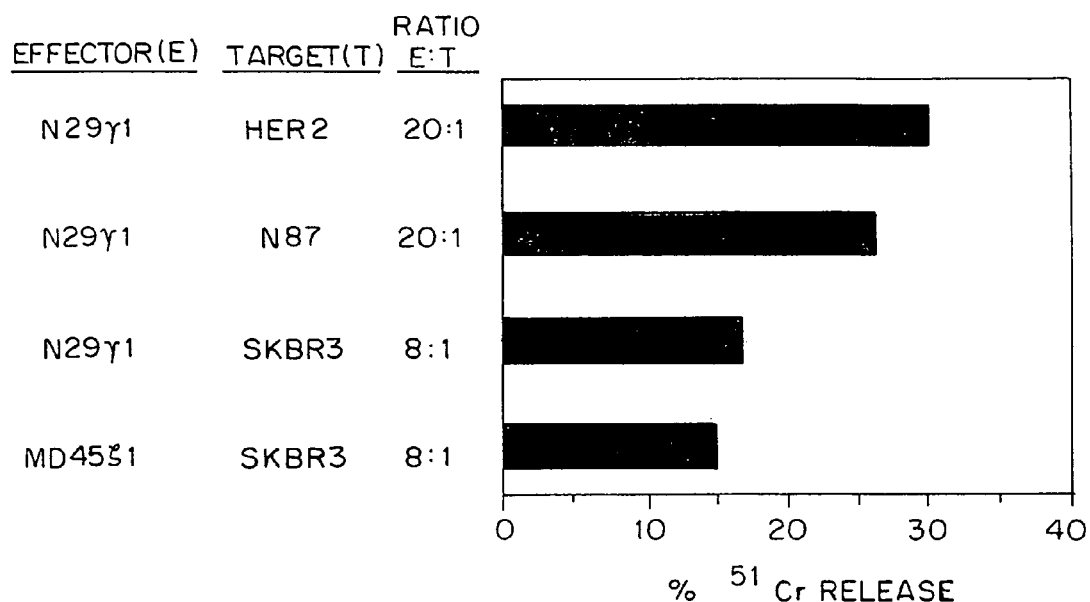

FIG. 11 shows that chimeric receptor expressing cells specifically lyse Neu/HER2 target cells. Non-transfected CTL hybridomas and the scFvN29Rγexpressing (N29γ1) or the scFvN29Rζ expressing (MD45ζ1) transfectants were studied for their cytolytic potential either toward Neu/HER2 expressing NIH-3T3 murine fibroblasts or the human gastric (N87) or breast (SKBR3) carcinoma cell lines. The percent $^{51}Cr$ released by the parental cells at the same E:T were subtracted.

Figure 12:
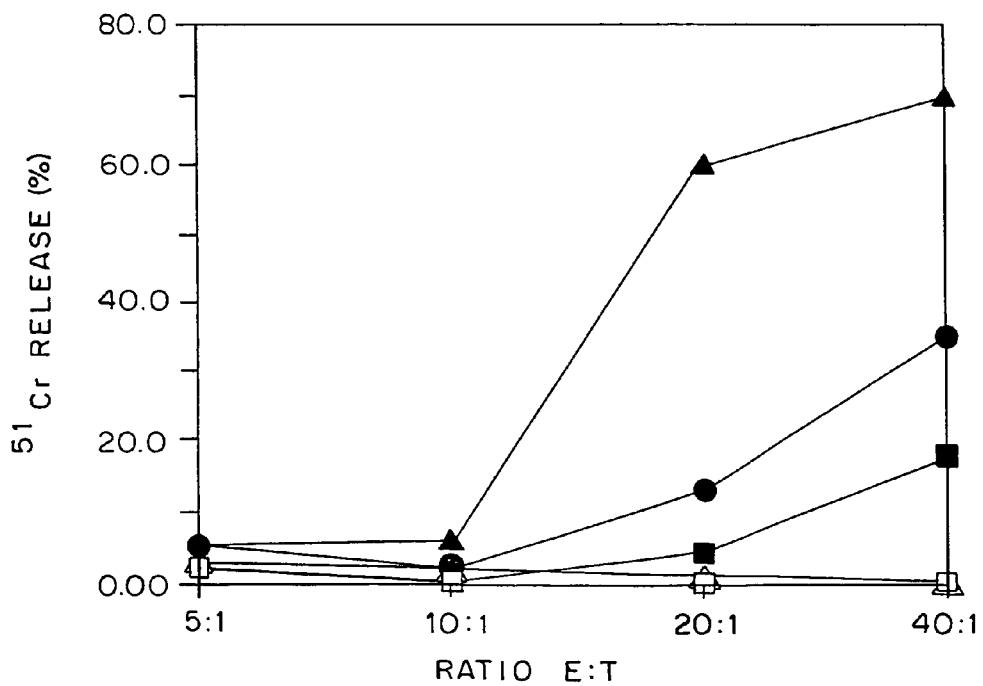

FIG. 12 shows that chimeric receptor expressing cells specifically lyse HER2 target cells. Non-transfected CTL hybridomas and the scFvN29Rγ expressing (N29γ1) or the scFvN29Rζ expressing (N29ζ18) transfectants were studied for their cytolytic potential either toward Neu/HER2 expressing NIH-3T3 murine fibroblasts (filled symbols) or the nontransfected NIH-3T3 cells (open symbols). Substantial and specific lysis of HER2 target cells was demonstrated by N29γ1 at all effector to target (E:T) ratios. Weak lysis of HER2 as compared to the untransfected fibroblasts was observed for N29ζ18, while the MD45 and MD45.27J, non-transfected hybridomas did not cause any significant $^{51}Cr$ release. [filled triangle], [empty triangle], -N29γ1; [filled circle]-N29ζ18; [filled square], [empty square]-MD45.27J.

Figure 13:
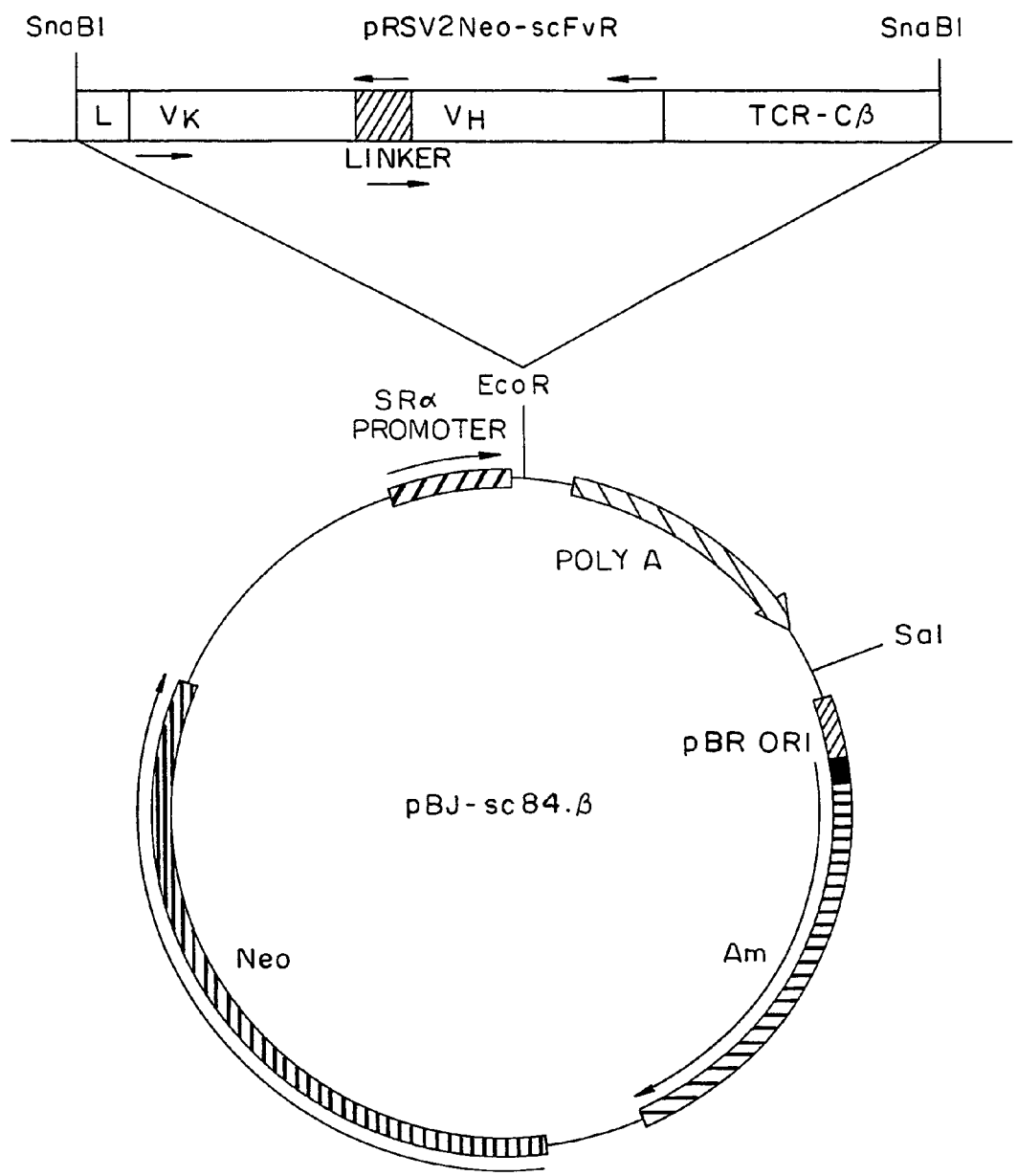

FIG. 13 shows transfer of the scFvR gene from the pRSV-neo-scFvR to the pBJ1-neo vector. The scFvR was cut out from the pRSV vector using the SnaBI and introduced into the EcoRV site of the polylinker of the pBJ1 plasmid to drive the expression of the chimeric gene from the SRα promoter.

Figure 14D:
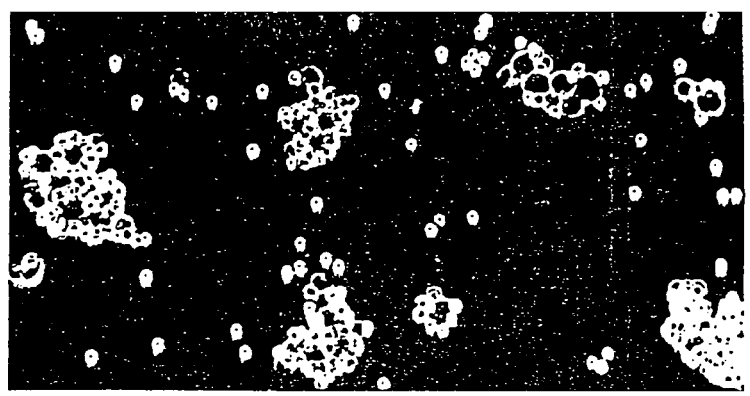
Figure 14E:
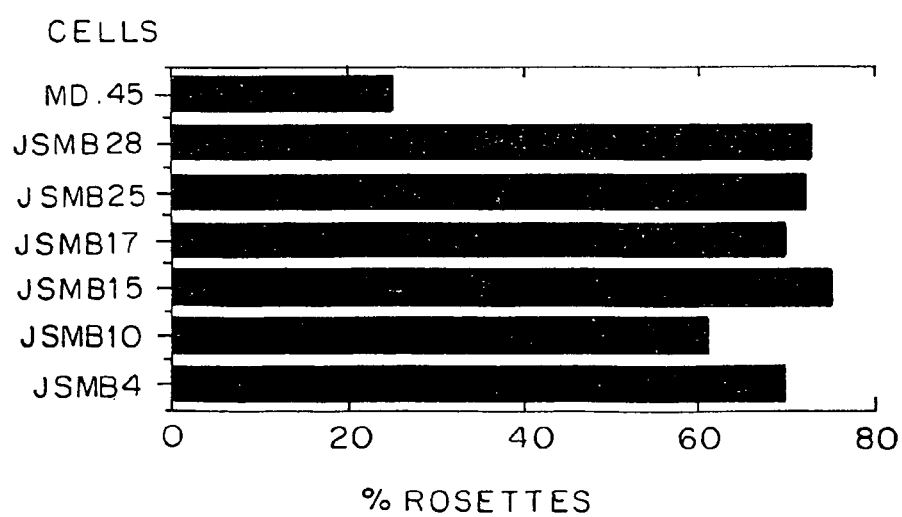

FIGS. 14A-14E. FIG. 14A shows schematic representation of rosette formation by T cells expressing the anti-IgE scFvCβ chimeric gene. Sheep red blood cells (HRBC) were coated with TNP and then with anti-TNP of the IgE class. The IgE-TNP-SRBC- complex was incubated with the T cells transfected with the scFvR comprising the scFv of the anti-IgE 84-1c mAb, and observed under microscope for rosette formation. FIG. 14B shows results of the rosette formation on scFvR-transfected JRT.T3.5 cells. parental JRT.T3.5 cells were used as negative and the 84.1c as positive controls. Results are given in percentage of cells that form rosettes. FIG. 14C shows inhibition, of rosette formation of transfectants expressing scFvR. The transfectants were incubated with IgE, anti-Fc and anti-MYC, IgG (as negative control) and then with the SRBC-conjugate and counted. FIG. 14D shows rosette formation of the JSB.15 transfectant. FIG. 14E shows rosette formation of the MD.45 derived transfectants expressing the scFvR.MD.45 was used as negative control.

Figure 15A:
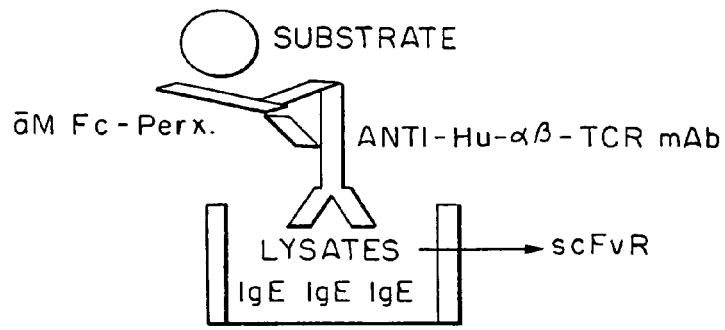
Figure 15B:
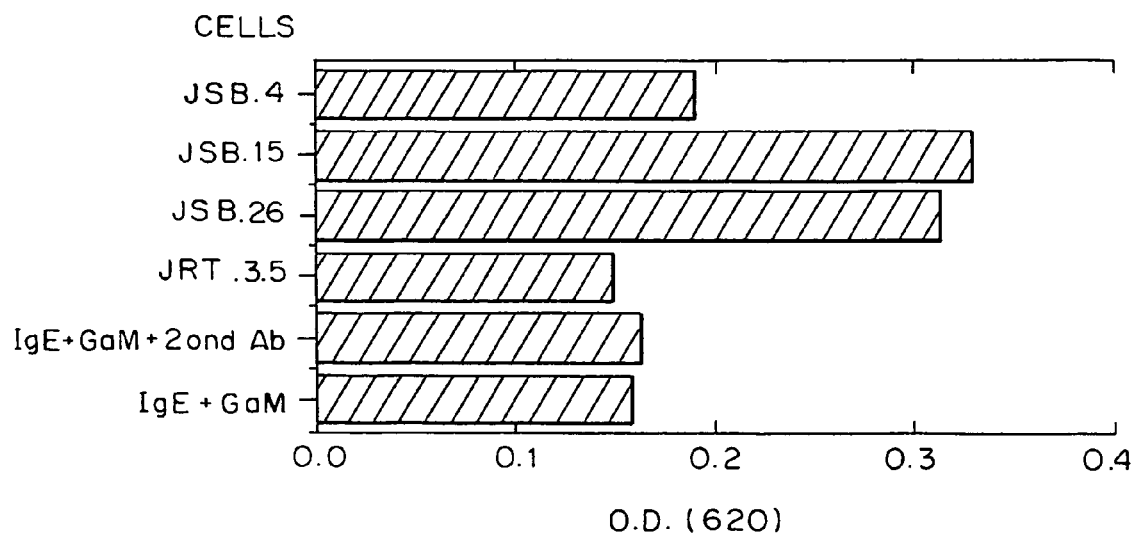

FIGS. 15A-15B. FIG. 15A shows schematic representation of the ELISA used to screen transfectants expressing scFvCβ chimeric gene (R is Cβ). Plates were covered with IgE and lysates of the transfectants were added, then anti-human α/β TCR antibodies were added and the reaction was developed with goat anti-mouse peroxidase. FIG. 15B shows results of some transfectants expressing the scFvR in the ELISA anti-human β TCR antibodies.

FIG. 16 shows stimulation of transfectants with immobilized IgE or anti-CD3 for IL-2 production. plates were coated with 2.5 µg/ml of either IgE or anti-CD3 purified antibodies and transfectant cells were incubated in the presence of phorbol 12-miristate 13-acetate (PMA), (10 ng/ml) for 20-24 hours. supernatants were collected and IL-2 production was determined using the IL-2 dependent cell line CTLL. Untransfected JRT.T3.5 cell was used as negative control and controls for the different media were also included in the CTLL assay.

Figure 17:
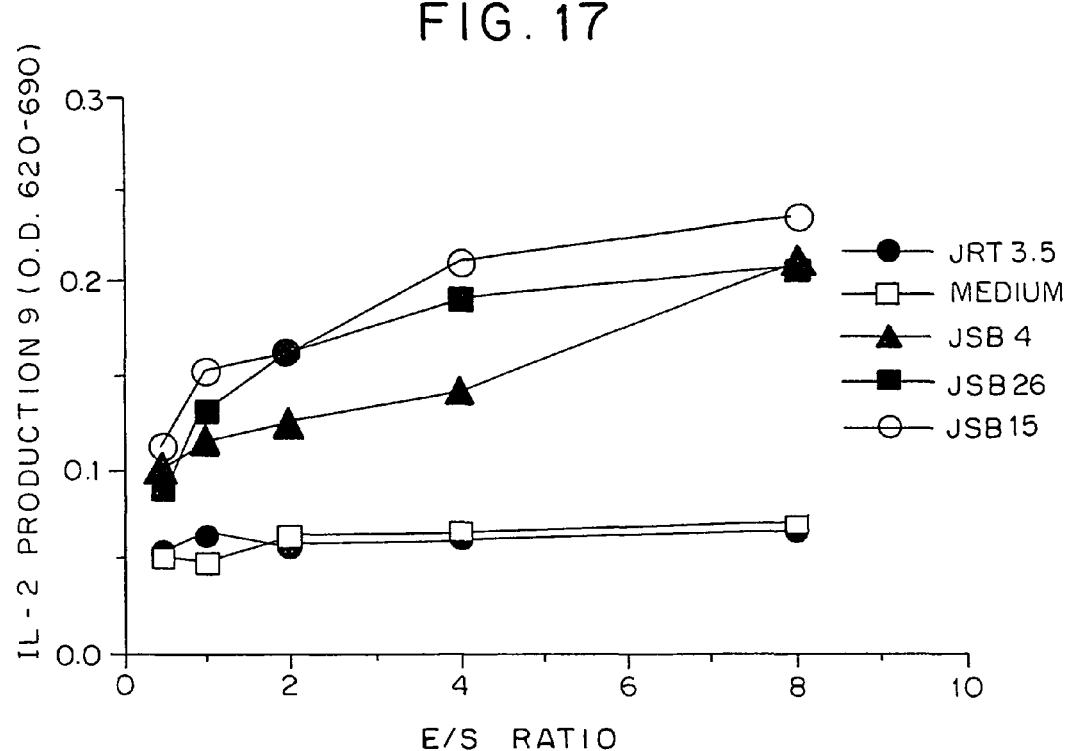

FIG. 17 shows stimulation for IL-2 production with IgE positive B cells. The SPE-7 IgE secretor hybridoma was fixed with 0.25% glutaraldehyde for 10 min. at 0° C. and mixed with the transfectants in different effector/stimulator (E/S) ratio. Cells were incubated for 20-24 hours and supernatants were collected and assayed for IL-2 production.

Figures 18A, 18B:
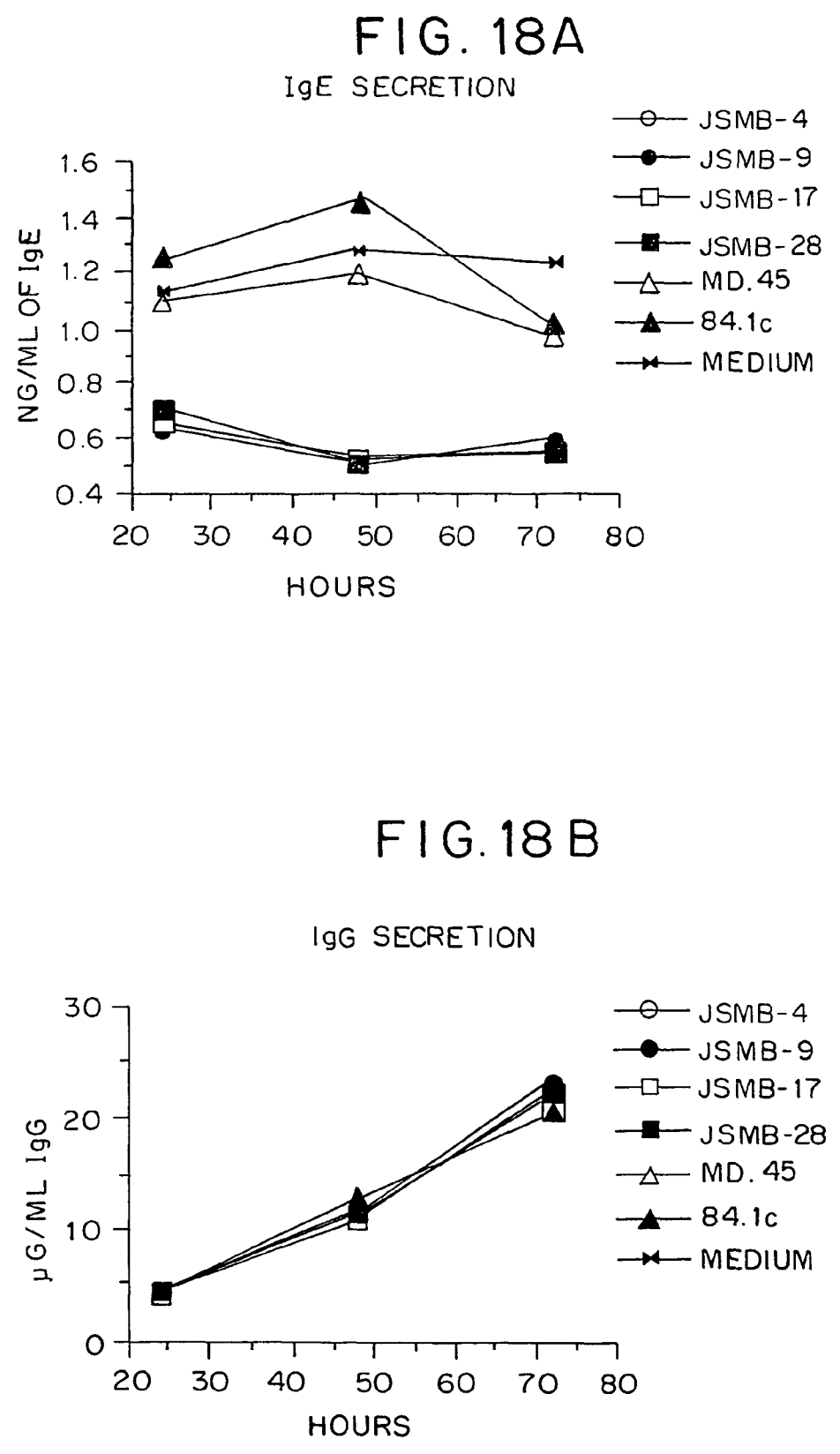

FIGS. 18A and 18B show specific inhibition of IgE production by cytotoxic hybridoma expressing the anti-IgE scFvR. Spleen cells were stimulated with 20 µg/ml LPS and 100 U/ml IL-4 for four days. At day 4 spleen cells were washed and MD.45 cytotoxic hybridoma expressing the scFv was added and IgE and IgG concentrations were measured after 24, 48 and 72 hours. 84.1c hybridoma cells were included as control as well as the MD.45.

Figure 19:
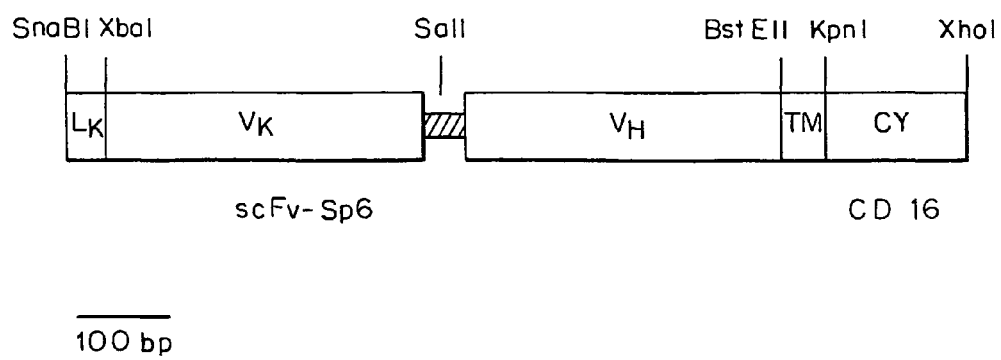
Figure 20A:
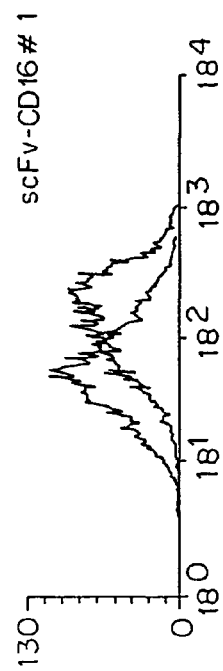
Figure 20C:
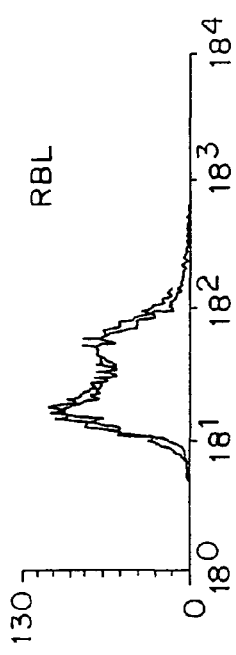
Figure 20B:
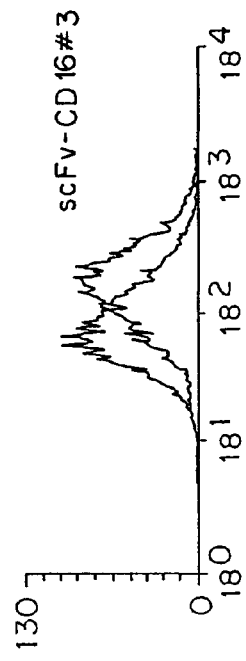
Figure 20D:
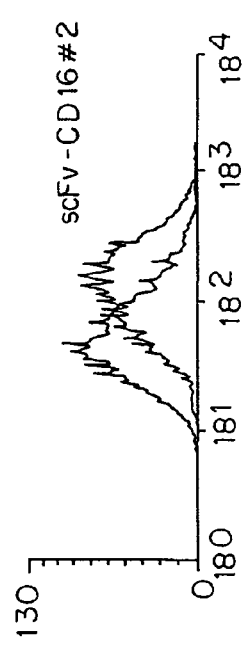
Figure 21A:
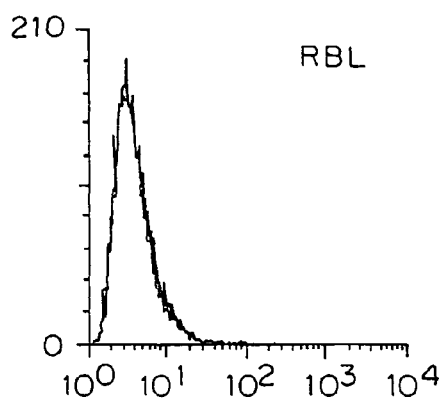
Figure 21B:
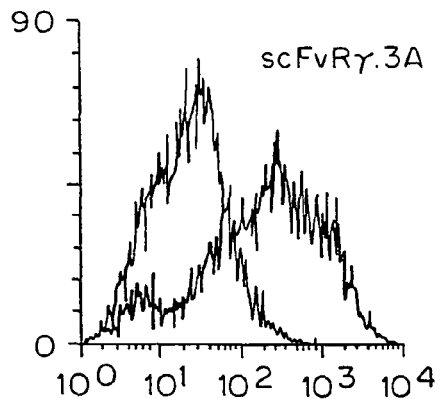
Figure 21C:
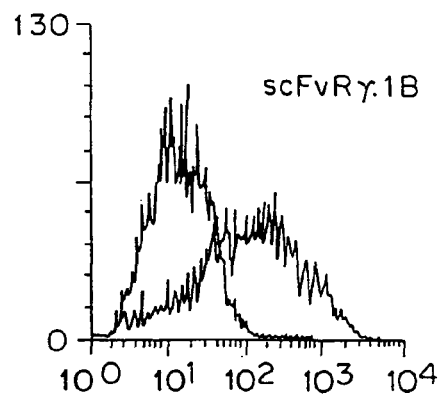
Figure 21D:
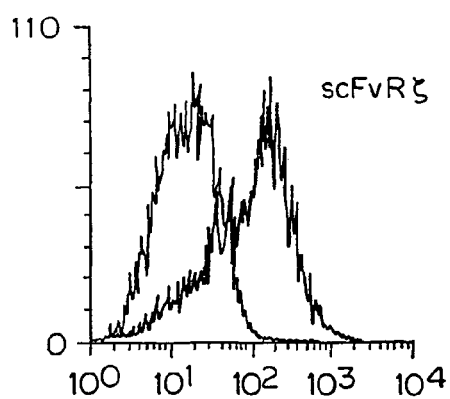

FIG. 19 is a schematic representation of the chimeric scFv-CD16 gene.

FIGS. 20A-20D show surface staining of rat basophilic leukemia (RBL) cells transfected with the scFvCD16 gene. Immunofluorescence staining was performed with anti-Sp6 idiotypic mAb 20.5 and irrelevant mouse antibody as negative control. The shift to the right in the FACS staining pattern is due to chimeric receptor expressing cells.

FIGS. 21A-21D show surface staining of RBL cells transfected with scFvRγ or scFvRζ chimeric genes. Immunofluorescence staining was performed with anti-Sp6 idiotypic mAb 20.5 and irrelevant mouse antibody as negative control.

FIGS. 22A and 22B show surface staining of murine thymoma BW5147 cells transfected with the scFvCD16 gene. Immunofluorescence staining was performed with anti-Sp6 idiotypic mAb 20.5 and irrelevant mouse antibody as negative control.

FIG. 23 shows stimulation of BW5147 cells co-transfected with scFvCD16 and normal γ chain by TNP-labeled A.20 target cells. BW-scFvCD16 clone 45 (A) or clone 50 (B) were co-cultured at different target: stimulation ratios with TNP modified irradiated A.20 cells. IL-2 produced into the supernatant was determined following 24 hours by the MTT assay.

Figure 24A:
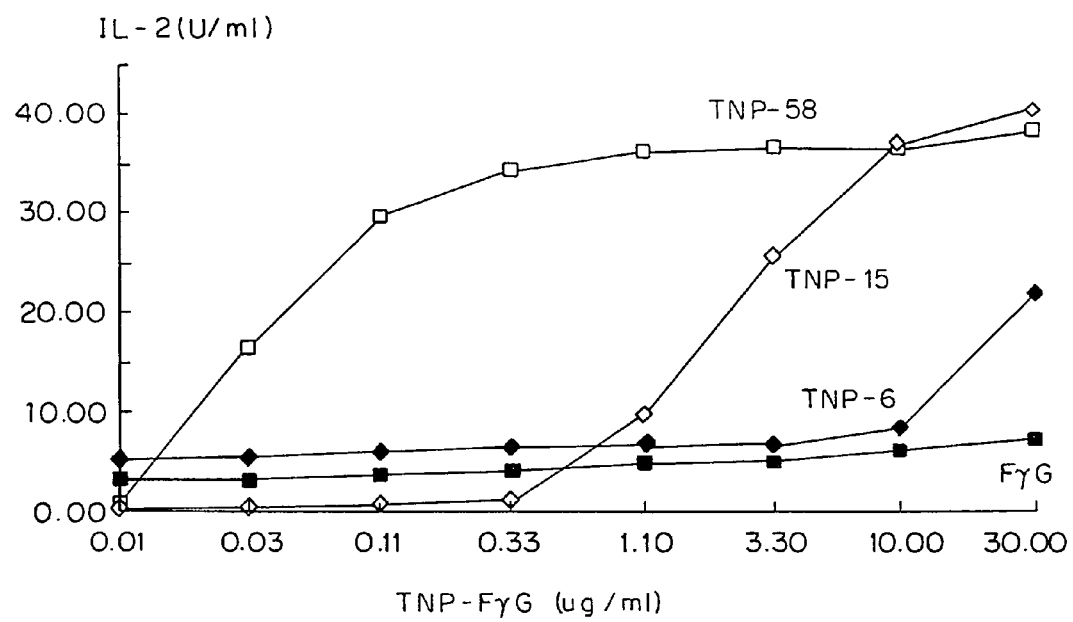
Figure 24B:
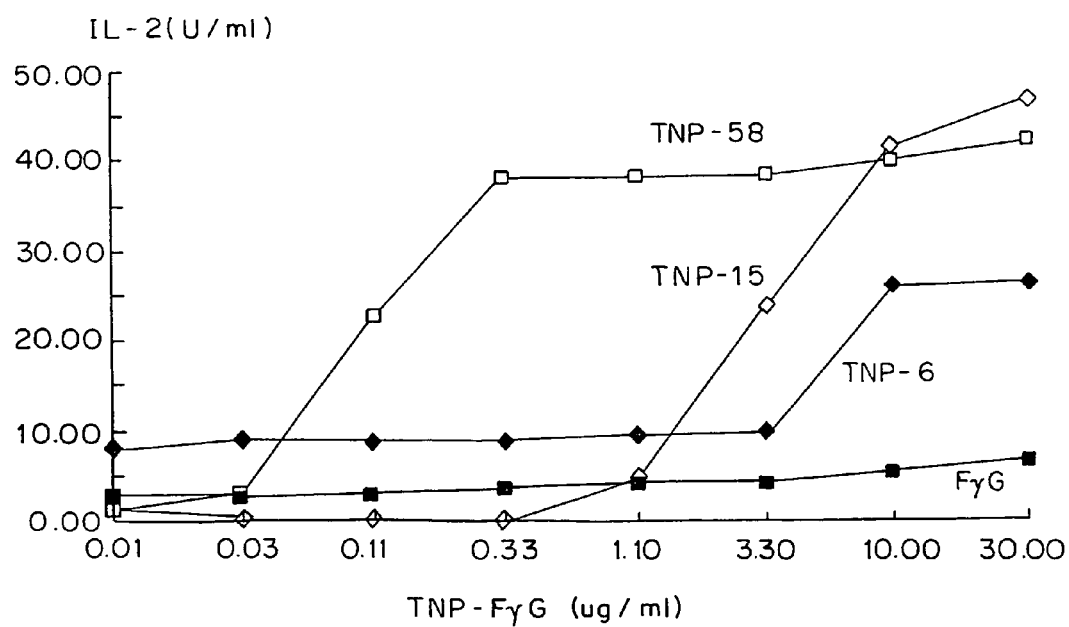
Figure 25A:
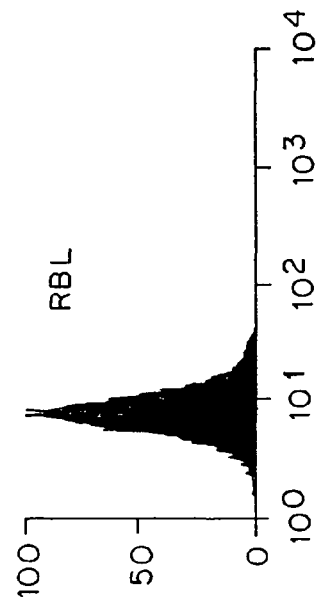
Figure 25B:
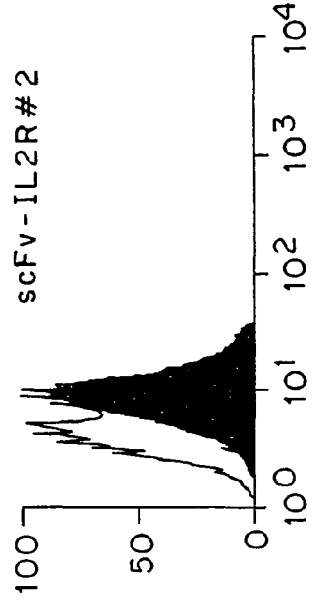
Figure 25C:
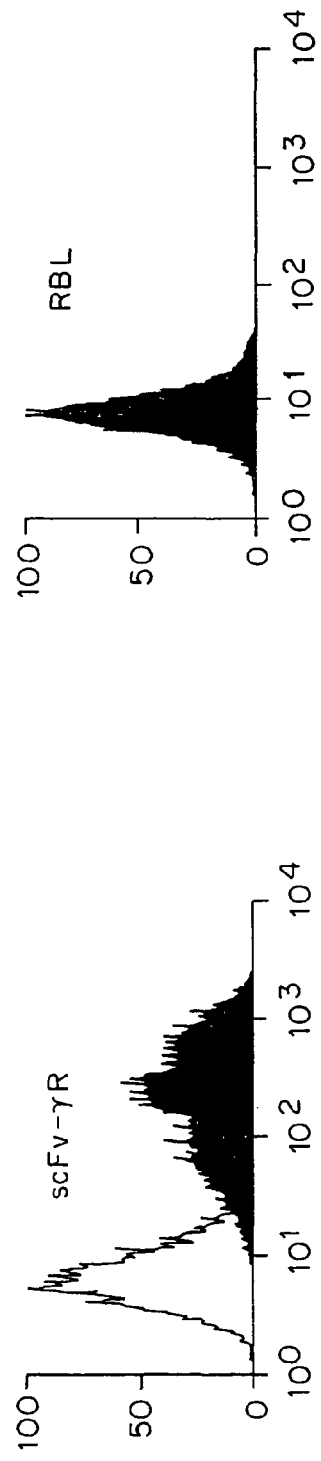
Figure 25D:
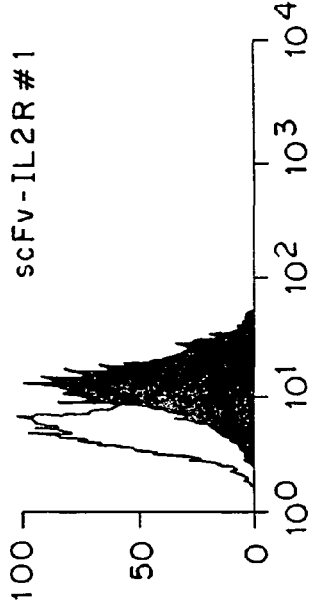
Figure 26B:
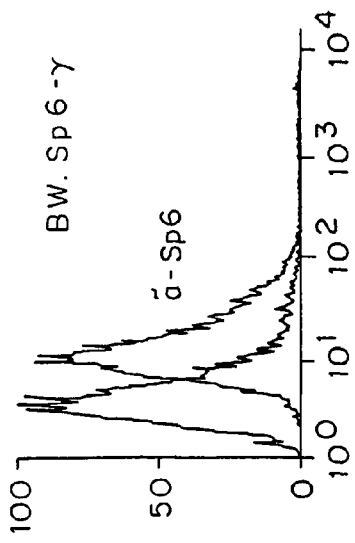
Figure 26D:
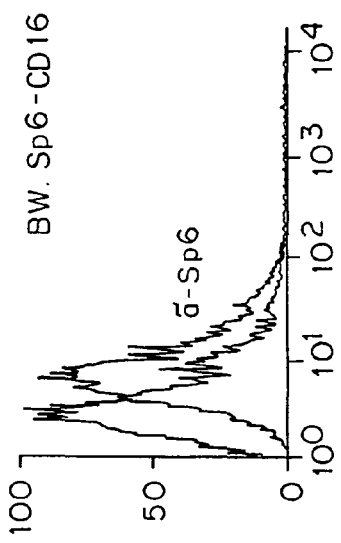
Figure 26A:
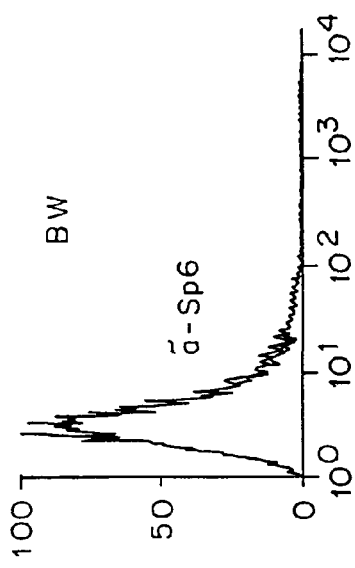
Figure 26C:
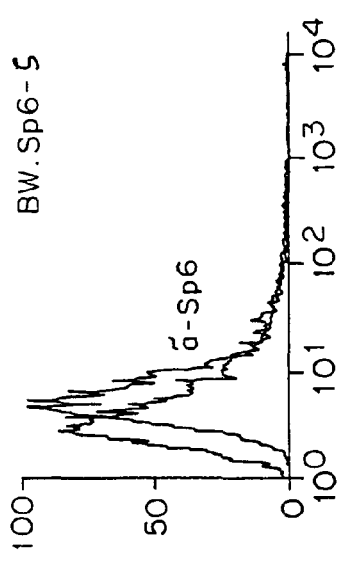

FIGS. 24A and 24B show stimulation of BW5147 cells cotransfected with scFvCD16 and normal γ chain by immobilized TNP-Fowl γ-globulin (TNP-FγG). Different concentrations of TNP-FγG at different TNP:FγG ratios were used to coat the wells of a microculture plate. IL-2 was determined in the supernatant of 24 hr cultures of BW-scFvCD16 clone 5 (FIG. 24A) or clone 50 (FIG. 24B). Incubation of either one of the cells with immobilized FγG by itself (filled squares) did not stimulate the cells. The parental BW cells did not make any IL-2 in response to TNP-FγG under the same conditions (not shown).

FIGS. 25A-25D show surface staining of RBL cells transfected with the scFvIL2R gene. Immunofluorescence staining was performed with anti-Sp6 idiotypic mAb 20.5 and irrelevant mouse antibody as negative control.

FIGS. 26A-26D show that BW5147 cells transfected with scFvR express surface chimeric receptors. BW5147 cells transfected with Sp6-scFvR were reacted with 1:200 dilution of ascites of 20.5 anti-Sp6 idiotypic antibody or anti-MOv18 ascites in the same dilution as control, followed by FITC labeled anti-mouse Ig. Immunofluorescence was detected by FACS. BW.Sp6-CD16 are cells co-transfected with scFvCD16 and γ chain. Cells transfected with scFvCD16 alone did not stain above the untransfected BW cells.

Figure 27:
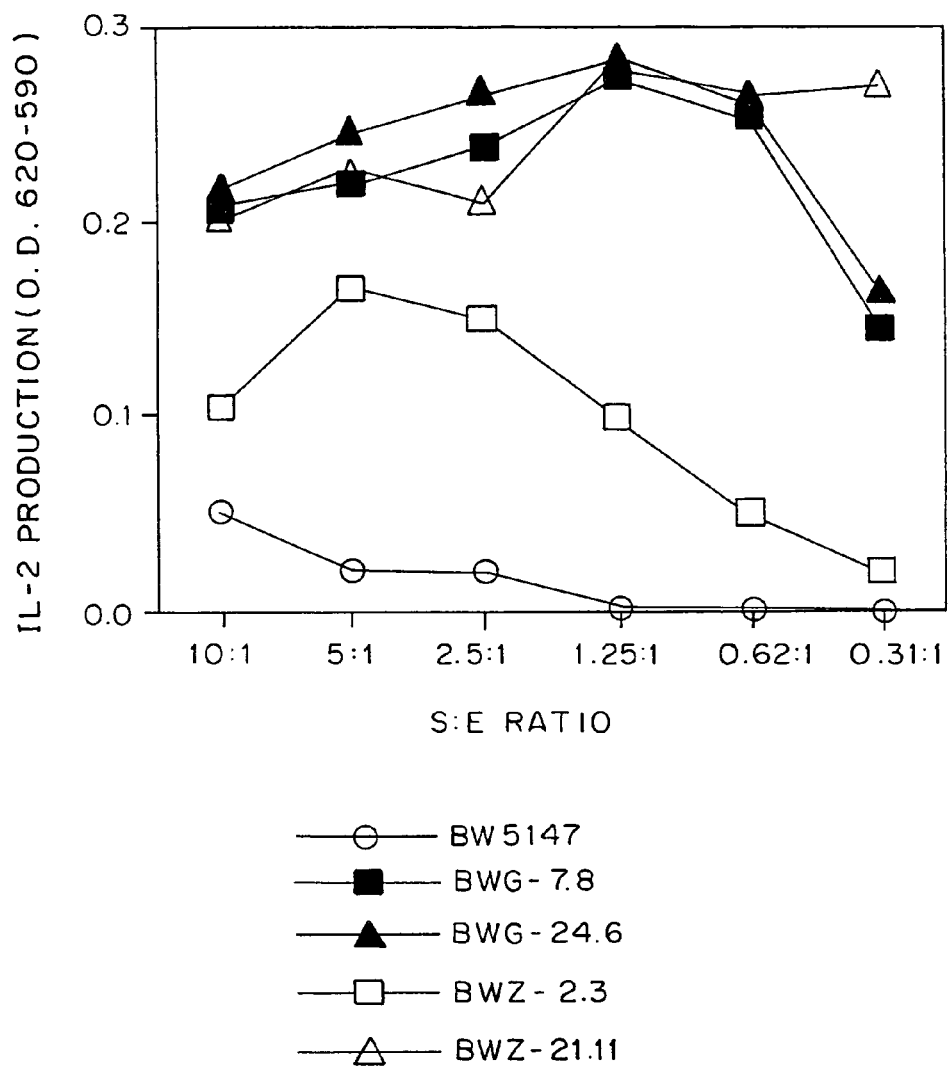

FIG. 27 shows stimulation of scFvR-BW5147 transfectants with TNP-A.20 cells. Different BW-scFvR transfectants were incubated with various amounts of TNP-A.20 cells for 24 hrs. IL-2 was determined by the MTT calorimetric assay. BWG are scFvRγ transfectants and BWZ are scFvRζ transfectants.

Figure 28:
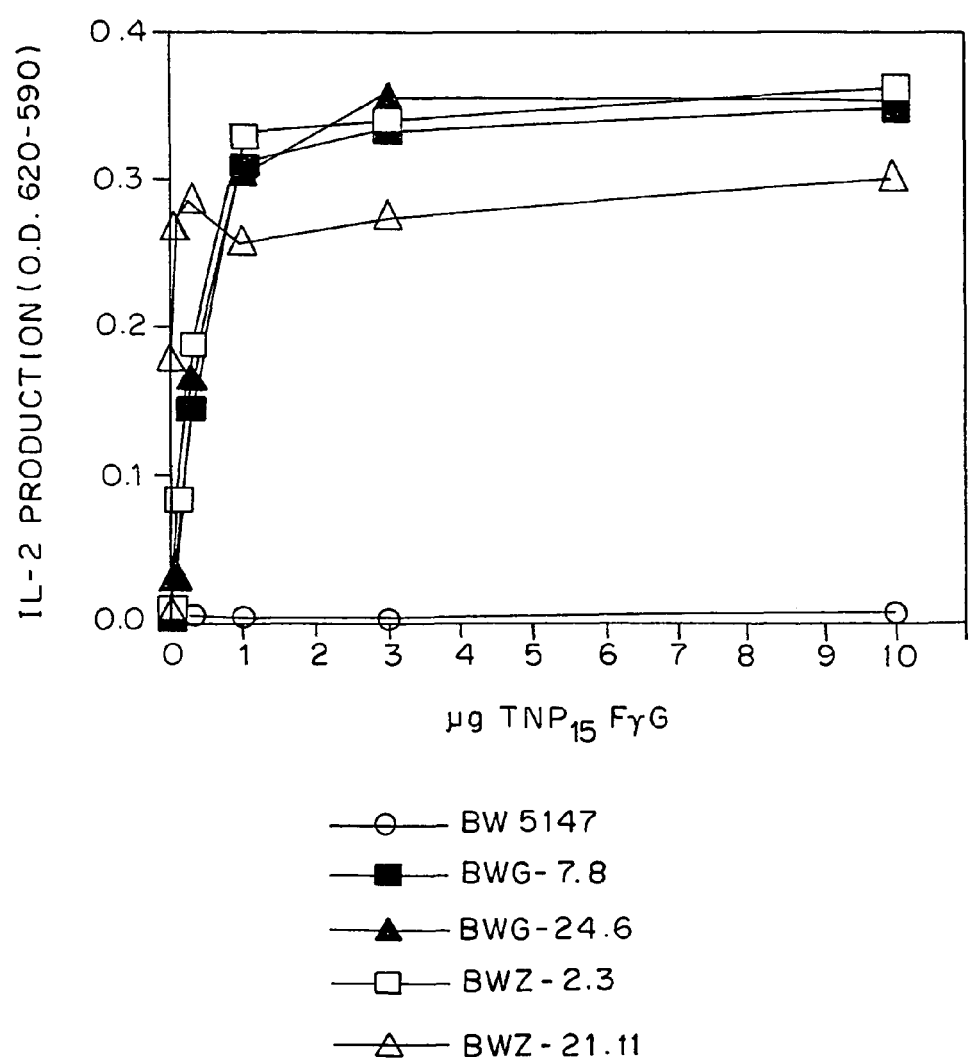

FIG. 28 shows that scFvR transfected BW5147 cells respond to immobilized TNP. Different BW-scFvR transfectants ware incubated with $TNP_{15}$-FγG coated wells for 24 hrs. IL-2 was determined by the MTT calorimetric assay. The abscissa describes the concentrations of TNP-FγG used to coat the wells of a microtitre plate. BWG are scFvRζ transfectants and BWZ are scFvRζ transfectants.

DETAILED DESCRIPTION OF THE INVENTION

To overcome the difficulties of the prior method involving the gene-pairs approach (the "T-body" approach) and to extend its applicability to other cells and receptor molecules, a new alternative design was developed according to the invention. It is based on a single-chain approach to the cTCR and on the demonstrated ability to express in bacteria an antibody single-chain Fv domain (scFv) (16, 17). Such scFv domains, which join the antibody's heavy and light variable ($V_H$ and $V_L$) gene segments with a flexible linker, have proven to exhibit the same specificity and affinity as the natural Fab' fragment. Thus, one immediate application of the scFv is to construct chimeric molecules composed of scFv linked to one of the TCR constant domains.

Figure 1:
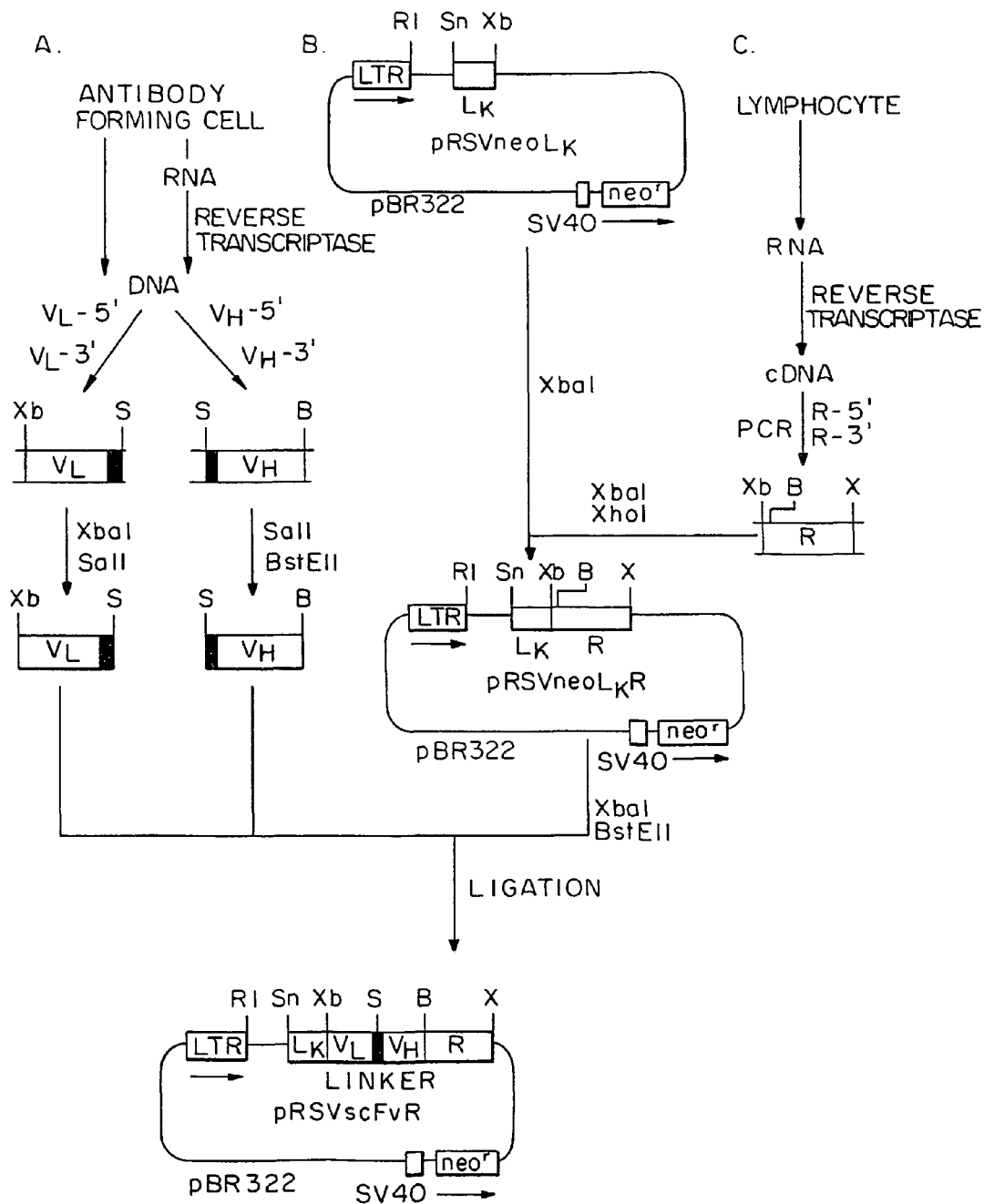
FIG. 1 depicts a scheme of the chimeric scFvR expression vector. R represents any receptor chain, such as the zeta subunit of the CD3, gamma and CD16$\alpha$ subunits of the FC$\gamma$RIII, C$\alpha$ and C$\beta$ of the TCR, $\beta$ chain of the IL-2 receptor or any other chain or part thereof described herein. A depicts the preparation of the gene segments encoding the scFv of the $V_H$ and $V_L$ of a specific antibody linked by a flexible linker (hatched box). B represents the pRSV expression vector containing the kappa light chain leader ($L_\kappa$), into which the receptor gene prepared from lymphocytes described in C and the gene segment of A are introduced. Expression of the chimeric gene is driven by the long terminal repeat (LTR) promoter of the Rous sarcoma virus.

According to the invention, chimeric molecules were constructed composed of the scFv linked to receptor subunits that might serve to transduce the signal from the scFv and confer antibody specificity to T cells as well as other lymphocytes. This construction is preferably accomplished in the manner shown in FIG. 1 at A, DNA or RNA from antibody forming cells is isolated. cDNA is prepared from mRNA and amplification of the antibody light and heavy variable regions ($V_H$ and $V_L$) by PCR using a $V_L$ -5' (XbaI), $V_L$-3 (SalI), $V_H$-5' (SalI) and $V_H$-3' (BstEII) specific primers. As shown at B, To the $pRSV_2$-neo plasmid a leader sequence from the S1C5 kappa chain was introduced down stream from the LTR promoter. At C, RNA from T lymphocytes was isolated and from the cDNA prepared the α, β chains of the TCR, γ, ζ subunits of the CD3, CD16α of the FCγRIII, or IL-2 receptors (commonly denoted here as R) can be amplified using a specific set of primers for each chain. All the primers include a XbaI at their 5' end and a few bases downstream of the XbaI or the BstEII site. At the 3' end, all receptor chains contain a SnaBI site. Following introduction of the leader sequence into the $pRSV_2$-neo plasmid the receptor was introduced at the XbaI site of the pRSVneoL$_K$ vector obtaining pRSVneoL$_K$-R. The amplified $V_L$ (digested with XBaI-SalI) and $V_H$ (digested with SalI-BstEII) regions are introduced into the XbaI-BstEII digested pRSVneoL$_K$-R plasmid in a three-piece ligation. The resulting plasmid pRSVscFvR contains the complete chimeric single chain receptor. The receptor (R) gene segment described in FIGS. 13-18 is the human TCR Cβ.

Thus, the new strategy according to the invention enables the use of other receptor molecules which might serve to transduce the signal from the scFv and confer antibody specificity to T cells as well as other immune cells. In fact, it allows the expression of the scFv as the antigen recognition unit of chimeric molecules composed of the transmembrane and cytoplasmic domains of receptor molecules of immune cells, such as T cells and natural killer (NK) cells. Such receptors can be single or multi-chain in nature and not necessarily belong to the Ig gene superfamily.

Candidate molecules for this approach are receptor molecules which take part in signal transduction as an essential component of a receptor complex, such as receptors which trigger T cells and NK activation and/or proliferation. Examples of triggers of T cells are subunits of the TCR, such as the α, β, γ or δ chain of the TCR, or any of the polypeptides constituting the CD3 complex which are involved in the signal transduction, e.g., the γ, δ, ε, ζ and η CD3 chains. Among the polypeptides of the TCR/CD3 (the principal triggering receptor complex of T cells), especially promising are the zeta and its eta isoform chain, which appear as either homo- or hetero-S—S-linked dimers, and are responsible for mediating at least a fraction of the cellular activation programs triggered by the TCR recognition of ligand (18, 19). These polypeptides have very short extracellular domains which can serve for the attachment of the scFv.

Additional examples of immune cell trigger molecules are any one of the IL-2 receptor (IL-2R) p55 (α) or p75 (β) or γ chains, especially the p75 and γ subunits which are responsible for signaling T cell and NK proliferation.

Further candidate receptor molecules for creation of scFv chimeras in accordance with the present invention include the subunit chains of Fc receptors.

In the group of NK-stimulatory receptors the most attractive candidates are the γ- and CD16α-subunits of the low affinity receptor for IgG, FcγRIII. Occupancy or cross-linking of FcγRIII (either by anti-CD16 or through immune complexes) activates NK cells for cytokine production, expression of surface molecules and cytolytic activity (20, 21). In NK cells, macrophages, and B and T cells, the FcγRIII appears as a heterooligomeric complex consisting of a ligand-binding α chain associated with a disulfide-linked γ or zeta chain. The FcγRIIIA signalling gamma chain (22) serves also as part of the FcεRI complex, where it appears as a homodimer, is very similar to the CD3 zeta chain, and in fact can form heterodimers with it in some cytolytic T lymphocytes (CTL) and NK cells (23-25). Most recently prepared chimeras between these polypeptides and the CD4 (26), the CD8 (27), IL-2 receptor chain (28) or CD16 extracellular domains, proved to be active in signalling T cell stimulation even in the absence of other TCR/CD3 components.

In addition to the receptor molecules discussed above, there are lymphocyte accessory and adhesion molecules such as CD2 and CD28, which transduce a co-stimulatory signal for T-cell activation. These co-stimulatory receptors can also be used in accordance with the present invention.

Besides the specific receptor chains specifically mentioned herein, the single chain Fv chimeras can be made by joining the scFv domain with any receptor or co-receptor chain having a similar function to the disclosed molecules, e.g., derived from granulocytes, B lymphocytes, mast cells, macrophages, etc. The distinguishing features of desirable immune cell trigger molecules comprise the ability to be expressed autonomously (i.e., as a single chain), the ability to be fused to an extracellular domain such that the resultant chimera is expressed on the surface of an immune cell into which the corresponding gene was genetically introduced, and the ability to take part in signal transduction programs secondary to encounter with a target ligand.

The scFv domain must be joined to the immune cell triggering molecule such that the scFv portion will be extracellular when the chimera is expressed. This is accomplished by joining the scFv either to the very end of the transmembrane portion opposite the cytoplasmic domain of the trigger molecule or by using a spacer which is either part of the endogenous extracellular portion of the triggering molecule or from other sources. The chimeric molecules of the present invention have the ability to confer on the immune cells on which they are expressed MHC nonrestricted antibody-type specificity. Thus, a continuous polypeptide of antigen binding and signal transducing properties can be produced and utilized as a targeting receptor on immune cells. In vivo, cells expressing these genetically engineered chimeric receptors will home to their target, will be stimulated by it to attract other effector cells, or, by itself, will mediate specific destruction of the target cells. In a preferred embodiment, the target cells are tumor cells and the scFv domain is derived from an antibody specific to an epitope expressed on the tumor cells. It is expected that such anti-tumor cytolysis can also be independent of exogenous supply of IL-2, thus providing a specific and safer means for adoptive immunotherapy.

In preferred embodiments, the immune cells are T-cells or NK-cells. The antibody scFvR design of the present invention will thus involve retargeting lymphocytes in vivo in an MHC-non-restricted manner. Thus, the T-cells can be re-targeted in vivo to tumor cells or any other target of choice toward which antibodies can be raised.

The term "single-chain Fv domain" is intended to include not only the conventional single-chain antibodies as described in references 16 and 17, the entire contents of which are hereby incorporated herein by reference, but also any construct which provides the binding domain of an antibody in single-chain form as, for example, which may include only one or more of the complementarity determining regions (CDRs), also known as the hypervariable regions, of an antibody.

The gene encoding the transmembrane and cytoplasmic portions of the receptor molecule may correspond exactly to the natural gene or any gene which encodes the protein in its natural amino acid sequence. Furthermore, the present invention comprehends muteins characterized by certain minor modifications to the amino acid structure of the molecule, such that the mutant protein molecules are substantially similar in amino acid sequence and/or 3D structure, and possess a similar biological activity, relative to the native protein.

The transformed cells of the present invention may be used for the therapy of a number of diseases. Current methods of administering such transformed cells involve adoptive immunotherapy or cell-transfer therapy. These methods allow the return of the transformed immune system cells to the blood stream. Rosenberg, S. A., *Scientific American* 62 (May 1990); Rosenberg et al., *The New England Journal of Medicine* 323(9):570 (1990).

The transformed cells of the present invention may be administered in the form of a pharmaceutical composition with suitable pharmaceutically acceptable excipients. Such compositions may be administered to any animal which may experience the beneficial effects of the transformed cell of the present invention, including humans.

Those of ordinary skill in the art will further understand that the antibodies which are used to make the scFv portion of the present invention may be any antibody, the specificity of which is desired to be transferred to the immune cell. Such antibody may be against tumor cells, cells expressing viral antigens, anti-idiotypic or anti-clonotypic antibodies in order to specifically eliminate certain B-cells and T-cells, or antibodies against the constant region of immunoglobulin determinants. Thus, for example, if the antibody is specific to the constant portion of IgE, it can serve to eliminate IgE-producing B-cells in order to alleviate allergy, etc. This list of possible antibodies is not intended to be exclusive and those of ordinary skill in the art will be aware of many additional antibodies for which important utilities exist upon combination with the receptor in accordance with the present invention.

The genes of the present invention can be introduced into the immune cells by any manner known in the art, such as, for example, calcium phosphate transfection, electroporation, lipofection, transduction by retrovirus vector, use of a retroviral vector or a viral vector, etc.

The scFvR design is advantageous over the cTCR one. It requires the expression of only one gene instead of the gene pair required for the cTCR, thereby providing simpler construction and transfection.

Furthermore, the scFvR design can be employed to confer antibody specificity on a larger spectrum of signaling molecules composed of only one chain. Additionally, the scFv maintains both $V_H$ and $V_L$ together in one chain; thus, even upon mixed pairing of chimeric with endogenous chains, the antigen-binding properties of the molecule are conserved. Finally, the fact that gamma and zeta constitute the signaling chains of the TCR/CD3, the FcγRIII and the FcεRI expands the feasibility of exploiting the chimeric receptor for retargeting other hematopoietic cells, such as NK cells, basophils, or mast cells in addition to T cells.

The chimeric scFvRγ of the invention or any of the simple modifications thereof described below, that combine the specificity of an antibody as a continuous single-chain and the effector function of cytotoxic T cells and NK cells or regulatory function of helper T cells, constitute an important consequential development for targeted immunotherapy. This approach exploits the scFv as the antigen-recognition unit and the potent cytotoxic responses of NK cells and T cells and/or the ability of T cells to secrete lymphokines and cytokines upon activation at the target site, thus recruiting, regulating and amplifying other arms of the immune system.

The chimeric scFv receptors can confer on the lymphocytes the following functions: antibody-type specificity toward any predefined antigen; specific "homing" to their targets; specific recognition, activation, and execution of effector function as a result of encountering the target; and specific and controlled proliferation at the target site. Endowing the lymphocytes with an Fv from an antibody may also serve for controlled and selective blocking of the aforementioned functions using soluble haptens or Fab' of anti-idiotypic antibodies.

Candidate immune cells to be endowed with antibody specificity using this approach are: NK cells, lymphokine-activated killer cells (LAK), cytotoxic T cells, helper T cells, and the various subtypes of the above. These cells can execute their authentic natural function and can serve, in addition, as carriers of foreign genes designated for gene therapy, and the chimeric receptor shall serve in this case to direct the cells to their target. This approach can be applied also to anti-idiotypic vaccination by using helper T cells expressing chimeric receptors made of Fv of antiidiotypic antibodies. Such "designer lymphocytes" will interact and stimulate idiotype-bearing B cells to produce antigen-specific antibodies, thus bypassing the need for active immunization with toxic antigens.

The invention will now be illustrated by the following non-limiting examples.

EXAMPLES

Example 1

Constructions and Expression of the Chimeric ScFvRγ/ζ Chain Genes

In this example, the following materials and methods were used.

A. Cell lines and antibodies. MD.45 is a cytolytic T-lymphocyte (CTL) hybridoma of BALB/c mice allospecific to H-2$^b$ (29). MD45.27J is a TCR α- mutant of MD.45. A.20 is a B lymphoma of BALB/c origin (ATCC#T1B 208). Cells were cultured in Dulbecco's modified Eagle's medium (DMEM) supplemented with 10% fetal calf serum (FCS). Sp6, an anti-TNP mAb, and 20.5, an anti-Sp6 idiotype mAb, were provided by G. Kohler (30). Anti-human FcεRIγ chain polyclonal and monoclonal (4D8) (31) antibodies were provided by J. -P. Kinet and J. Kochan, respectively, and rabbit antibodies to murine zeta chain by M. Baniyash.

Figure 2:
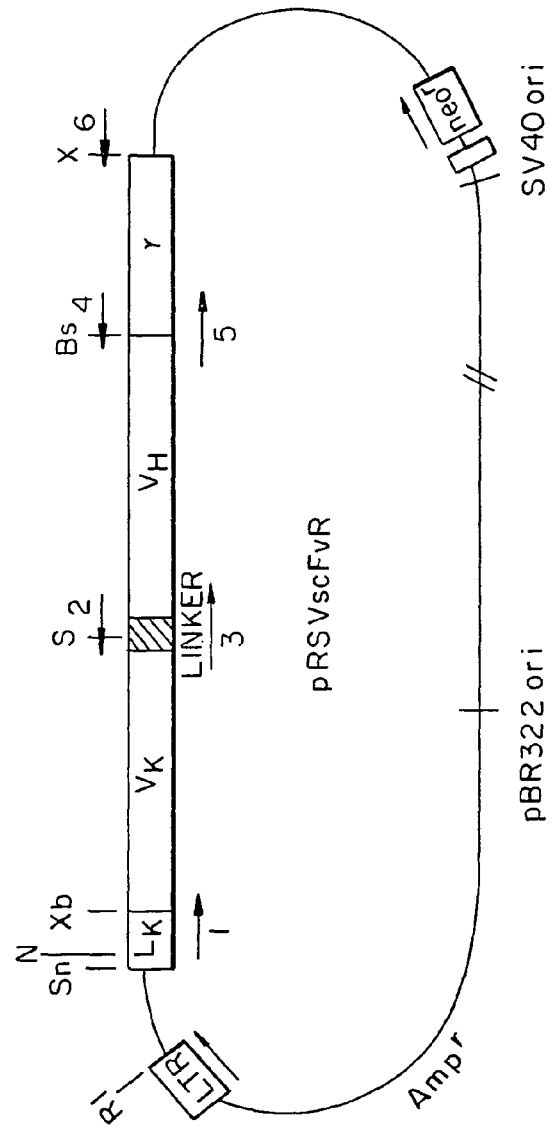
FIG. 2 illustrates the chimeric pRSVscFvR$\gamma$ expression vector obtained according to the scheme of FIG. 1. The boxes from left to right represent DNA segments corresponding to the Rous sarcoma virus long terminal repeat promoter (LTR), kappa light chain leader ($L_\kappa$) and variable region ($V_\kappa$), the linker (hatched box), heavy chain variable region ($V_H$) the human gamma chain, the G418-resistance gene (neo$^r$) and the simian virus 40 origin of replication. Restriction sites indicated are EcoRI (RI), SnaBI (Sn), NcoI (N), XbaI (Xb), SalI (S), BstEII (Bs), and XhoI (X). The arrowheads numbered 1 to 6 represent the flanking regions amplified by using the oligonucleotide primers 4, 5, 6, 7, 14 and 15, respectively shown in Table I, infra.

B. Constructions of chimeric genes. All the recombinant DNA manipulations were carried out as described in updated editions of Sambrook et al. (1989) *Molecular Cloning: A Laboratory Manual*, Cold Spring Harbor, N.Y., and Ausubel et al. (1987) *Current Protocols in Molecular Biology*, John Wiley & Sons. The specific genes encoding the $V_H$ and $V_L$ Of the Sp6 anti-TNP antibody were derived from the genomic constructs described for the preparation of the cTCR (12, 32) by PCR amplifications using oligodeoxynucleotide primers designed according to the 5' and 3' consensus amino acid sequences of immunoglobulin V regions (33) introducing the Xba I and BstEII restriction sites at the ends of the scFv. In constructing the scFv we used the $V_L$-linker-$V_H$ design containing a linker sequence similar to linker 212 described by Colcher et al. (34). Accordingly, the $V_L$-3' and the $V_H$-5' primers include sequences comprising the 5' and 3' parts of the linker, introducing Sal I in their 3' and 5' ends, respectively. Table I lists the oligonucleotide primers used in the different constructions. In the examples, reference is made to the number of the specific primer used. Following digestion of the purified PCR products with Xba I and Sal I ($V_L$) and Sal I and BstEII ($V_H$), the fragments were ligated into the Xba I and BstEII sites of a pRSV2neo-based expression vector containing the leader of S1C5 kappa light chain (provided by S. Levy) and TCR constant region β chain (Cβ), prepared for the expression of anti-38C.13 cDNA cTCR genes (12). The Cβ of this plasmid was then replaced with either the gamma chain amplified from a human cDNA clone (35) or the zeta chain amplified from Jurkat cDNA by using primers introducing BstEII and Xho I at the 5' and 3' ends. A schematic diagram of the final scFvRγ expression vector is depicted in FIG. 2. The sequences of the oligodeoxynucleotide primers used for the construction of the chimeric scFvRγ and scFvRζ are delineated Table 1.

TABLE I

Primers used for construction of the various scFvR

Base code

| R = A or G | S = C or G | TACGTA SnaBI | GTCGAC SalI | GGATCC BamHI |
|---|---|---|---|---|
| Y = C or T | K = G or T | CTCGAG XhoI | GGTGACC BstEII | AAGCTT HindIII |
| W = A or T | M = A or C | TCTAGA XbaI | GAATTC EcoRI | GGTACC KpnI |

Primers for cDNA Reverse Transcription

| SEQ ID NO 1 | mouse C$_\gamma$1 | 5' GGCCAGTGGATAGAC 3' |
|---|---|---|
| SEQ ID NO 2 | mouse kappa | 5' GATGGTGGGAAGATG 3' |
| SEQ ID NO. 3 | rat C$_\gamma$3 | 5' CCATGRYGTATACCTGTGG 3' |

Primers for Single chain Fv

| SEQ ID NO 4 | V$_\kappa$-5' | 5' CCCGTCTAGAGGAGAYATYGTWATGACCCAGTCTCCA 3' |
|---|---|---|
| SEQ.ID NO 5 | V$_\kappa$-3' | 5' CCCGTCGACCCTTTWATTTCCAGCTTWGTSCC 3' |
| SEQ ID NO 6 | V$_H$-5' | 5' CGGGTCGACTTCCGGTAGCGGCAAATCCTCTGAAGGCAAAGGTSAGG 3' |
| SEQ ID No 7 | V$_H$-3' | 5' TGMRGAGACGGTGACCGTRGTYCCTTGGCCCCAG 3' |

Receptor primers

| SEQ ID NO 8 | 5' Cα (XhoI) | 5' CCTCGAGATAAAAAATATCCAGAACCCTGACCCTGCC 3' |
|---|---|---|
| SEQ ID NO 9 | 5' Cα (BstEII) | 5' CGGTCACCGTCTCCTCAAATATCCAGAACCCTGACCCTGCC 3' |
| SEQ ID NO 10 | 5' Cβ (XhoI) | 5' CCTCGAGATAAAAGAGGACCTGAAAAACGTGTTCCCA 3' |
| SEQ ID NO 11 | 5' Cβ (BstEII) | 5' CGGTCACCGTCTCCTCAGAGGACCTGAAAAACGTGTTCCCA 3' |
| SEQ ID NO 12 | 3' TCRα | 5' TACGTATCAGCTGGACCACAGCCGCAGCGTCAT 3' |
| SEQ ID.NO. 13 | 3' TCRβ | 5' TACGTATCAGCCTCTGGAATCCTTTCTCTTGAC 3' |
| SEQ ID NO 14 | 5' FcRγ | 5' CCGGTCACCGTCTCTTCAGCGGATCCTCAGCTCTGCTATATCCTGGA 3' |
| SEQ ID.NO. 15 | 3' FcRγ | 5' GGCAGCTGCTCGAGTCTAAAGCTACTGTGGTGG 3' |
| SEQ ID NO. 16 | 5' TCRζ | 5' GCTGGATCCCAAACTCTGCTACC 3' |
| SEQ ID.NO. 17 | 3' TCRζ | 5' CGCCTCGAGCTGTTAGCGAGGGGGC 3' |
| SEQ ID.NO. 18 | 5' CD16 | 5' CCGGTCACCGTCTCCTCAGGGTACCAAGTCTCTTTCTGC 3' |
| SEQ ID.NO. 19 | 3' CD16 | 5' CCCTCGAGTCATTTGTCTTGAGGGTC 3' |
| SEQ.ID.NO. 20 | 5' IL-2Rβ | 5' CCGGTCACCGTCTCTTCAGCGGATCCTACCATTCCGTGGCTCGGCCA 3' |
| SEQ.ID NO 21 | 5' IL-2Rβ | 5' GGAGATAGAAGCTTGCCAGG 3' |
| SEQ ID NO 22 | 3' IL-2Rβ | 5' CCTGGCAAGCTTCTATCTCC 3' |
| SEQ ID.NO 23 | 3' IL-2Rβ | 5' GGCTCGAGTCTACACCAAGTGAGTTGGG 3' |

C. Expression of the Chimeric scFvRγ/ζ genes. Transfection of 20 μg of pRSVscFvRγ/ζ DNA into 20×10$^6$ MD.45 or MD.27J hybridoma cells was performed by electroporation using an ISCO power supply at 1.9 kV (32). Transfectants were selected in G418 at 2 mg/ml. Expression of scFvRγ/ζ on the surface of transfected cells was evaluated by immunofluorescence staining using the 20.5 anti-Sp6 idiotype and fluorescein-isothiocyanate (FITC)-labelled anti-mouse Fab' antibody. Functional assays included an IL-2 production assay and a cytotoxicity assay in which the ability of transfectants to respond specifically to TNP-modified A.20 target cells was evaluated as detailed in Ref 9. The amount of IL-2 was determined by using an IL-2-dependent CTL line and methyl tetrazolium acid (MTT) staining (36). Cytotoxicity assay was monitored by $^{51}$Cr release (29). All determinations were performed in triplicate.

D. Immunoprecipitation and Immunoblotting. Washed pellets containing 10$^8$ cells were lysed in 1 ml of 1% digitonin, 0.12% Triton X-100 in 10 mM Tris.HCl—saline buffer pH 7.4 containing 10 mM EDTA, 1 mM phenylmethyl sulfonyl fluoride (Sigma), 10 μg/ml aprotinin and 10 μg/ml leupeptin (Boehringer Mannheim, GmbH). After 20 min at 0° C. and centrifugation at 12000×g for 15 min, aliquots of the supernatants were incubated with antibodies and then precipitated with second antibodies and Protein G-Sepharose (Pharmacia) as described (32). Alternatively, cell lysates were mixed with sample buffer to a final concentration of 1% NaDodSO$_4$ and either 10 mM iodoacetamide (for non-reducing gels) or 15 mM dithiothreitol (for reducing gels). The washed immunoprecipitates were dissociated in sample buffer under the same conditions. To avoid destruction of the Sp6 idiotope, the samples were incubated at 20° C. for 30 min before NaDodSO$_4$/PAGE through 5-20% gel gradient. Separated proteins were blotted onto nitrocellulose paper and allowed to react with anti-Sp6, anti-gamma or anti-zeta antibodies followed by peroxidase-labelled anti-immunoglobulin antibodies. Washed blots were developed by using a chemiluminescence kit (ECL, Amsterdam) according to the manufacturer's recommendations, and exposed to film (Kodak, X-OMAT AR).

E. Results. To produce a chimeric receptor with an antigen binding site of a given antibody and the signalling gamma or zeta chains, we have adopted the scFv design (16, 17) which allows combining both entities into one continuous molecule. In engineering the pRSVscFvRγ/ζ expression vector (FIGS. 1,2), harboring the V$_L$ and V$_H$ of the Sp6 anti-TNP mAb (37), we introduced elements that enable its usage as a modular expression cassette to accommodate scFvs from different antibodies in combination with gamma, zeta or other chains. This was achieved by using oligonucleotide primers composed of sequences common to the majority of the 5' and 3' sequences of either V$_L$ or V$_H$ regions, flanked by relatively unique restriction sites, which allow both in-frame ligation of the different units and its removal to other vectors (see Table I). We have chosen to use the 5'-V$_L$-linker-V$_H$-3' design, which was found suitable for the expression of a variety of single-chain antibodies and their fragments in bacteria (17), but the converse, 5'-V$_H$-linker-V$_L$-3', alignment (16) can be used as well.

Introduction of the chimeric scFvRγ gene into the MD.45 murine CTL hybridoma (STA series of transfectants) or its MD45.27J TCRα- mutant, which does not express surface TCR/CD3 complex (STB series), resulted in the expression of the chimeric molecule on the cell surface of selected clones as revealed by staining with the anti-Sp6 idiotypic antibody (FIG. 3). Similar staining was observed for STZ, which was derived by transfecting MD45.27J with the scFvRζ chimeric gene. The surface expression of the scFvRγ or scFvRζ molecule was independent of the TCR/CD3 complex; it did not restore surface expression of the CD3 in MD45.27J transfected STB or STZ cells, and some subclones of the STA that initially expressed both scFvRγ and TCR/CD3 on their surface lost, upon a prolonged culture period, the TCR/CD3 expression without any apparent effect on the scFvRγ expression and function (not shown).

Immunoblotting analysis of cell lysates prepared from representative STA and STB transfectants using either antiidiotypic mAb 20.5 or polyclonal anti-human gamma antibodies, revealed 4 distinct bands of apparent molecular weight of 36, 54-62, 74-80 and 85-90 kDa, which did not appear in the parental cells (FIGS. 4A and 4B). Under reducing conditions one species, which corresponds to the predicted 36 kDa monomeric form of the scFvRγ, was apparent, indicating the multimeric nature of the molecule. The band with apparent 75 kDa molecular weight corresponds to the homodimeric molecule, and the nature of the 90 kDa species is unknown. It might represent a novel gamma-associated polypeptide, analogous to the one recently reported (31). This species can be detected only in immunoblots of cell lysates and is not apparent after surface iodination and immunoprecipitation (FIG. 5B), suggesting the intracellular origin of the molecule. The appearance of bands in the range of 54-62 kDa was more pronounced in the STB transfectant. It might represent heterodimers between the chimeric scFvRγ chain and endogenous zeta and probably eta chains of the CD3 complex. We therefore electrophoresed anti-Sp6 immunoprecipitates made from STB lysates, blotted the gels, and developed it with anti-Sp6, anti-gamma or anti-mouse zeta/eta antibodies (FIG. 5A). Both the anti-idiotypic and the anti-gamma antibodies revealed the four bands from the transfected cells; however, the anti-zeta (which cross-reacts with the mouse eta chain) differentially developed only the 60 kDa species. Immunoprecipitation of surface-iodinated proteins with either anti-Sp6 or anti-gamma antibodies (FIG. 5B) demonstrates a main species of 75 kDa under non-reducing conditions. This is the homodimer of the chimeric chain.

Example 2

Expression of scFvRγ/ζ as Functional Receptors

To test whether the chimeric scFvRγ or scFvRζ can function as an active receptor molecule, we studied the ability of the transfected hybridomas to undergo antigen-specific stimulation. The MD.45 T cell hybridoma can be triggered through its TCR to produce IL-2, IL-3 or GM-CSF. It specifically recognizes and responds to H-2$^b$ target cells (29), while its MD45.27J mutant cannot be stimulated through its TCR due to the absence of an α chain. Upon introduction of the chimeric Sp6-scFvRγ, both of these cells could be specifically triggered to produce IL-2 following incubation with TNP-modified stimulator cells (FIG. 6A) or plastic-immobilized TNP-fowl gamma globulin (TNP-FγG) (FIG. 6B). Non-modified A.20 cells or FγG did not activate the transfectants, demonstrating the specificity of the response toward TNP. Stimulation of the various transfectants with immobilized antigen resulted in different degrees of reactivity. While STA responded to plastic-bound TNP-FγG in consistent manner, STB and STZ (transfected with the scFvRγ and scFvRζ, respectively) lost their ability to undergo stimulation with immobilized antigen but not with hapten-modified cells. Such behavior suggests the necessity of additional synergistic signals for these cells. Indeed, costimulation with TNP-FγG plus either phorbol 12-myristate 13-acetate (PMA) or Ca$^{++}$ ionophore resulted in enhancement of IL-2 production (data unshown). Incubation with soluble TNP-proteins even at high hapten/protein ratios did not result in activation but rather specifically inhibited triggering by immobilized antigen (FIG. 6B) or cell-bound hapten. The activation of GTAe.20, a transfectant expressing a two-chain chimeric TCR (9), was also inhibited by soluble TNF-FγG. Identical concentrations of antigen were needed to cause 50% inhibition (IC$_{50}$) of STA and GTAe.20 (FIG. 6B), indicating that the single-chain and the double-chain Fv display the same relative affinity to TNP.

Finally, we tested the ability of the chimeric receptors to mediate specific target cell lysis by incubating them with $^{51}$Cr labeled cells. As shown in FIGS. 7A and 7B, only the cells transfected with the Sp6-scFvRγ or -scFvRζ could lyse TNP-modified target cells in a dose-related fashion. This cytolytic activity was specific to TNP as soluble TNP-FγG blocked it (not shown) and unmodified A.20 cells were not affected by the transfectants.

It is demonstrated here for the first time that a single-chain Fv of an antibody molecule fused to the gamma chain of the immunoglobulin Fc receptor or to the zeta chain of the CD3 complex can be expressed in T cells as an antigen-specific receptor. The chimeric scFvRγ/ζ endowed T cells with antibody-type specificity, transmitted a signal for IL-2 production and mediated target cell lysis. The demonstration that the scFvRγ/ζ fusion protein could mediate antigen-specific stimulation of T cells not expressing the TCR/CD3 receptor complex (as shown for the STB and STZ transfectants derived from the TCR-negative MD.27J mutant (FIGS. 5A-5B and 6A-6B), strongly suggests that the gamma and zeta chains are capable of autonomous activation of T cells. Yet, because of the low level of heterodimers between the scFvRγ and the endogenous zeta and eta chains (FIGS. 3 and 4A-4D), the possibility of some contribution by the residual zeta (or eta) chain in the signalling process cannot be excluded. Nonetheless, the present results clearly indicate that the TCR chains do not take part in this process, thus confirming and complementing recent observations in which antibody cross-linking through the extracellular domains of CD4, CD8, IL-2 receptor, or CD16 joined to the cytoplasmic tail of either one of the gamma/zeta family members resulted in T cell activation (26-28). Like scFvRγ/ζ chimeric CD4 or CD16-gamma/zeta molecules expressed in cytotoxic lymphocytes could direct specific cytolysis against appropriate target cells (26, 38). Analysis of mutations within the intracellular 18-residue motif, which has been recently assigned to account for the activity of the gamma/zeta chain, revealed that the ability to mediate calcium responsiveness can be separated from the ability to support cytolysis (38). This opens new possibilities in which the chimeric chain, composed of scFv and genetically modified zeta or gamma chains can be used not only to direct the specificity but also to dictate the selected reactivity of lymphocytes.

The finding that immobilization of antigen is needed for efficient stimulation through scFvRγ/ζ and that soluble multimeric ligand (such as TNP-protein) did not trigger, but rather inhibited, reptor-mediated activation through cell- or plastic-bound TNP (FIG. 5B), indicates that mere engagement or even cross-linking of adjacent gamma or zeta chains does not result in T cell activation (as manifested by IL-2 release). The dependence on ligand immobilization for efficient T cell triggering has been reported also for cTCR-mediated signalling (8, 9), and the mechanisms underlying this are as yet unclear. Using the hybridoma transfected cells, different variants were obtained which differ in their ability to respond to immobilized antigen or to TNP-modified stimulator cells of various origin. Because these variants express surface receptors and respond to stimuli which bypass the TCR (such as with PMA+Ca++ ionophore), it was reasoned that they are deficient in one of the components along the pathway leading to the costimulatory signal, required for optimal cytokine release (39). Indeed, the fact that the addition of either PMA or ionomycin to the immobilized antigen increased the response of most of these clones (not shown), strongly support this assumption.

Example 3

Targeting of Cytolytic Lymphocytes to Neu/HER2 Expressing Cells Using Chimeric Single-Chain Fv Receptors Cell surface molecules essential for the transformed phenotype or growth of malignant cells are attractive targets for anti-cancer immunotherapy. Antibodies specific to Neu/HER2, a human adenocarcinoma-associated growth factor receptor, were demonstrated to have tumor inhibitory capacity. Yet, the inefficient accessibility of antibodies to solid tumor limits their clinical use. To redirect effector lymphocytes to adenocarcinomas, we constructed and functionally expressed in T cells chimeric single-chain receptor genes incorporating both the antigen binding domain of anti-Neu/HER2 antibodies and the γ or ζ signal transducing subunits of the T cell receptor/CD3 and the immunoglobulin Fc receptor complexes. Surface expression of the anti-Neu/HER2 chimeric genes in cytotoxic T cell hybridomas endowed them with specific Neu/HER2 recognition enabling their activation for interleukin-2 production and lysis of cells overexpressing Neu/HER2. These chimeric genes can be used for the immunotherapy of cancer.

To establish the feasibility of the chimeric receptor approach to retarget cytolytic lymphocytes to tumor cells, we have used anti-Neu/HER2 antibodies. The Neu/HER2 (also called c-erbB-2) is a protooncogene product that encodes a growth factor receptor implicated in the malignancy of several human adenocarcinomas that overexpress it. Out of a panel of monoclonal antibodies mAbs) specific to the extracellular portion of the Neu/HER2 protein (41), we selected mAb N29 which significantly inhibited the tumorigenic growth of HER2/Neu transfected fibroblasts in nude mice, and induced phenotypic differentiation of various cultured breast cell lines (42). In this example, we show that T cells equipped with anti-Neu/HER2 specificity as the ligand binding domain of the chimeric receptor, respond specifically to Neu/HER2 bearing target cells.

In this example, the following materials and methods were used.

A. Cells and Antibodies. MD45 a murine allospecific CTL hybridoma (29) and MD45.27J, its mutant lacking the TCR α chain, served as recipients for the chimeric genes. Stimulator and target cells used were human breast carcinoma cell lines SKBR3 and MDA 468, the human ovarian carcinoma cell line SKOV3, or HER2, a c-erbB-2 transfected 3T3-NIH fibroblasts (kindly provided by Dr. A. Ullrich). Cells were cultured in DMEM containing 10% FCS. N29 is a monoclonal anti-HER2 antibody (41), deposited with the Collection Nationale de Cultures de Microorganismes, Institut Pasteur, Paris France, on Aug. 19, 1992, under Registration No. CNCM I-1262. Anti-N29 idiotypic antiserum was prepared by immunizing rabbits with purified N29 protein and adsorption of the immune serum on a normal mouse Ig-agarose column. Rabbit anti-CD3ζ and anti-FcεRIγ antibodies were kindly provided by Dr. J. -P. Kinet.

B. Construction and Transfection of Chimeric Genes. Chimeric scFvN29Rγ or scFvN29Rζ genes were constructed from single chain Fv DNA (in the $V_L$-linker-$V_H$ alignment), amplified by PCR from cDNA prepared of hybridoma producing the N29 anti-HER2 mAb, and either γ or ζ genes as described in Example 1 for the anti-TNP scFvR. The MD45 or MD45.27J hybridomas were transfected by electroporation with 20 μg of DNA of pRSV2neo expression vectors harboring the chimeric genes and were selected for growth in the presence of 2 mg/ml G-418 (GIBCO) for 2-3 weeks as detailed in (9). Transfected cells were stained with either control serum or anti-N29 idiotypic antiserum (prepared by immunizing rabbits with purified N29 protein and adsorption of the immune serum on a normal mouse Ig-Agarose column. Following incubation at 4° C. with a 1:200 dilution of sera, the cells were washed and treated with fluorescein isothiocyanate-labeled goat anti-rabbit antibody (Jackson Labs, West Grove, Pa., USA) for an additional hour at 4° C. Immunofluorescence of individual cells was determined with a FACSCAN (Becton Dickinson).

C. Detection of Soluble Receptor. Cell lysates were prepared from the transfectants by adding 100 μl of lysis buffer composed of 1% Triton X-100 in 0.15 M NaCl-10 mM Tris.HCl pH 7.4 buffer containing 10 mM EDTA, 1 mM phenylmethyl sulfonyl fluoride (Sigma), 10 μg/ml aprotinin and 10 μg/ml leupeptin (Boehringer Mannheim, GmbH) to a pellet of $5 \times 10^6$ cells. After 30 min. at 0° C. and centrifugation, the nuclei-free supernatant was added to wells of a microtitre plate precoated with 5 μg/well of purified HER2X protein. HER2X is a recombinant extracellular domain of Neu/HER2 produced by CHO cells which were kindly provided by Dr. A. Ullrich. Following incubation for 2-4 hours at 4° C., plates were washed and incubated with 1 μg/ml of anti-human ζ or γ antibodies. After washing and the addition of horseradish peroxidase labeled anti-Ig antibodies (Jackson Labs), peroxidase substrate was added and the degree of binding was determined by reading the $OD_{690}$.

D. IL-2 Production and Cytotoxic Assays. Stimulator cells ($3 \times 10^4$/well) were cultured in 96-well microculture plates for at least 6 hours until adherent. For stimulation of transfectants with purified HER2X, wells of a microculture plate were coated with HER2X protein at the indicated concentrations for at least 3 h at 22° C. and then washed twice with medium. The transfected clones and their parental hybridoma were then added ($10^5$/200 μl/well) in DMEM supplemented with 10% fetal calf serum and $10^{-5}$ M of 2-β-mercaptoethanol. Following 20-24 hrs in culture, the amount of IL-2 produced was evaluated by the proliferation of the IL-2 dependent CTL-L cell line by the MTT calorimetric assay as previously described (9). To measure the cytotoxic activity, the transfectants and their parental hybridomas were co-incubated with $^{51}$Cr labeled target cells at various effector to target ratios for 16 hrs. The $^{51}$Cr release assay was performed as described previously (16).

E. Results. Genes coding for single chain Fv of N29 fused to either human γ or ζ chains were prepared in the pRS-VscFvR vector, and used to transfect the murine MD45 allospecific CTL hybridoma or its TCR α-mutant MD45.27J which does not express the TCR/CD3 complex. Surface expression of the chimeric chains on the hybridoma cells was detected using anti-idiotypic antibodies specific to the N29 anti-Neu/HER2 mAb (FIGS. 8A-8D). The integrity of the fusion protein comprising the antigen binding and signal transducing moieties was verified by a receptor-specific, enzyme-linked immunosorbent assay (ELISA), using a recombinant extracellular domain of Neu/HER2 (denoted HER2X) and anti-γ and ζ antibodies. As shown in FIGS. 9A-9B, specific binding to HER2X was observed in whole cell lysates of the transfected but not of the untransfected parental cells. Three transfectants, N29γ1 and N29γ15; both derived from MD45.27J cells transfected with the scFvRγ chimeric gene, and N29ζM.1, a derivative of MD45 cells transfected with the scFvRζ chimeric gene, were selected for functional studies.

The single-chain chimeric receptor was found to transduce specific signals for T cell activation. Incubation of the scFvR-expressing cells together with human cancer cells, which express Neu/HER2 on their surface, resulted in a marked activation as measured by the production of IL-2 (FIG. 10A). This activation was mediated by the scFvR and was Neu/HER2-specific, since cells which do not overexpress Neu/HER2, like MDA-MB468 human breast carcinoma cells, did not stimulate the production of high levels of IL-2, whereas cells that display large amounts of Neu/HER2, like the breast carcinoma SKBR-3 cells, ovarian carcinoma SKOV-3 cells and an erbB-2 transfected murine fibroblast cell line, stimulated the hybridomas to produce high IL-2 levels. Soluble, purified HER2X partially blocked the activation by the breast carcinoma cells. However, upon immobilization, it served as a potent T cell activator, but only for the transfected cells (FIG. 10B). The T cell response to the immobilized antigen was in general weaker than to the cellular targets. Possibly, co-stimulatory signals provided by accessory and adhesion molecules during T cell interactions may amplify the intercellular interaction.

Finally, the ability of the transfected cells to mediate specific target cell killing was determined by the $^{51}$Cr release assay. When a variety of Neu/HER2 expressing cells were tested as targets (FIG. 11), we found that the HER2 cell line, an NIH-3T3 fibroblast overexpressing Neu/HER2, could serve as an adequate target. Following incubation with an scFvRγ-expressing T cell hybridoma (N29γ1) (FIG. 12), a substantial level of specific lysis was obtained. The scFvRζ expressing hybridoma (N29ζ18) gave only a marginal specific $^{51}$Cr release signal when compared with the untransfected hybridomas. The cytolytic effect was Neu/HER2-specific, since untransfected NIH-3T3 fibroblasts did not undergo killing. Likewise, the parental MD45.27J cells did not cause any significant $^{51}$Cr release. The high levels of spontaneous $^{51}$Cr release from several candidate human tumor lines that we tested, did not allow us to determine the killing potency in a reproducible manner. Nevertheless, in all experiments, the transfected cells induced a significantly higher specific $^{51}$Cr release from human tumors (such as SKBR-3 breast and N87 gastric carcinoma cell lines, FIG. 11), than the parental hybridomas.

This study demonstrates that T cells expressing chimeric receptor genes utilizing single-chain Fv of anti-tumor antibodies can be redirected to tumor cells. Binding of the scFvR to the tumor antigen either in its isolated, immobilized form or in a cellular context was sufficient to trigger T cell activation and mediate target cell lysis. These results extend the previous examples using the anti-TNP scFvRγ/ζ. In all these instances, activated T cells or T cell lines have been used.

Example 4

Functional Expression of scFvR With Anti-IgE Specificity

Allergic diseases are characterized by elevated synthesis of IgE upon stimulation by environmental allergens. The production of IgE is regulated by antigen specific helper and suppressor T cells. T lymphocytes following activation, induce B cells to produce IgE. The secreted IgE binds preferentially to high affinity FCε receptors (FcεRI) on mast cells and basophils, thus sensitizing them. Following encountering allergen the FcεRI-bound IgE is cross-linked and stimulates exocytosis of granule-associated preformed pharmacologic mediators such as histamine. Elimination of IgE producing cells can therefore terminate IgE production and thus prevent the onset of allergic responses. In this example, we take advantage of the fact that both IgE producing cells and their B-cell precursors express surface IgE and by employing the "T body" strategy using chimeric single-chain T cell receptor (scFvR) genes, made of an Fv of anti-IgE antibodies, we can specifically block IgE production. The present example demonstrates the feasibility of this approach in an in vitro system, utilizing anti-mouse IgE antibodies.

In this example, the following materials and methods were used.

A. Generation and transfection of anti-IgE specific scFvR genes. The antibody which has been chosen is 84.1c, a rat mAb specific to an epitope on the murine Cε3 (43). The advantage of using 84.1c mAb is that it reacts with free IgE and not with mast-cell bound IgE, thus it was reasoned that it recognizes an epitope closely related to the FcεRI binding site on IgE. The basic strategy for construction of the chimeric genes encoding the 84.1c mAb $V_L$ and $V_H$ in a continuous single chain Fv linked to the constant region of the TCR α or β chains (Cα or Cβ) is similar to the one described for the preparation of the anti-TNP scFvRγ/ζ chimeric genes and is schematically described in FIGS. 1 and 2. mRNA was selected on oligo (dT) cellulose from the 84.1c hybridoma. Single strand cDNA was synthesized using a $3'C_\kappa$ and $3'C_H$ heavy primers employing M-MLV-reverse transcriptase (BRL). We amplified the $V_H$ and $V_\kappa$ by PCR using the mouse consensus oligonucleotide primers similar to the ones described above for the Sp6 anti-TNP scFv (44). The $V_\kappa$-3' primer and the $V_H$ -5' primer (5 and 6 of Table I) included sequences comprising the 5' and the 3' parts of the linker, introducing a Sal I site in their 3' and 5' ends, respectively. Following digestion of the purified PCR product with Xba I and Sal I ($V_\kappa$) and Xba I and BstE II ($V_H$), the fragments were ligated and introduced into the Xba I and BstE II sites of pRSVL$_\kappa$Cα or Cβ expression cassettes. These expression cassettes have been originally designed to express the double chain chimeric TCR (cTCR) genes (45, 9, 32) and were constructed by cloning into the pRSV$_2$neo the leader of the 38c.13 κ-light chain 3' to the RSV LTR and downstream, either the Cα or Cβ of the human TCR. The Cα and Cβ were PCR-amplified from human TCR clones using primers 9 and 12 from Table I for Cα and 11 and 13 for Cβ. Because we found previously (46) that the SRα promoter (47) drives transcription in T cells better than the RSV LTR, we adopted it here for the anti-IgE scFvR expression. For this purpose, we used the pBJ1neo plasmid (47). We cut out the complete scFv at the SnaBI sites from the pRSVscFvCβ/Cα vectors and introduced it into the EcoRV of the pBJ1neo vector. FIG. 13 describes the construction of the SRα based vector (pBJ-sc84.β).

The 84.1c based scFvCβ chimeric gene was introduced into either the murine MD45 hybridoma (29) or the human Jurkat T cell leukemia β TCR negative JRT3.5 mutant (48), respectively. Transfection was carried out by electrophoresis and transfectants were selected in the presence of 2 mg/ml G418 as described in (9). JRT.T3.5 derived transfectants with the scFvR are denoted JSB and the MD.45 transfectants-JSMB.

B. Expression of the anti-IgE scFvR in T cells. To determine the integrity of the chimeric genes, their ability to encode for surface receptor and to study the molecular nature of the receptor, we first transfected the Cβ based chimeric gene into the human leukemic Jurkat cell mutant JRT3.5, lacking the TCR β chain. In the absence of anti-84.1c idiotype antibodies, we screened the transfectants obtained for the reappearance of surface CD3 by immunofluorescence, using anti-CD3 antibodies, expecting that the chimeric scFvCβ chain will associate with the endogenous TCR α chain and bring out the TCR/CD3 complex. Although in parallel experiments we could bring out the CD3 to the surface of JRT3.5 cells following transfection with $V_HC\alpha$ or $V_LC\alpha$ cTCR chains, we could not demonstrate any CD3-specific staining of transfectants receiving the scFvCβ gene (data unshown). We therefore monitored surface expression of the chimeric scFv genes in the transfectants by rosette formation using trinitrophenylated sheep red blood cells (TNP-SRBC) coated with anti-TNP IgE SPE-7 (49). FIGS. 14A-14E represents such experiments depicting the rosettes and showing that they are specific to IgE and could be inhibited by adding IgE (and not control IgG antibody, FIG. 14C). That the chimeric receptors contain both the antigen-binding moiety and TCR determinants in the same complex, was shown by analyzing lysates made of the transfectants. Incubation of such cell-free lysates on IgE-coated wells, followed by the addition of anti-TCR-β specific mAbs and peroxidase labeled anti-mouse Ig antibodies, yielded specific binding (FIGS. 15A-15B).

C. Functional expression. Transfectants expressing chimeric surface receptors were tested for their ability to undergo specific activation for IL-2 production following stimulation with IgE, either immobilized by coating onto the plastic of the culture well or as a surface protein on IgE-producing hybridoma. FIG. 16 shows experiments in which the transfected cells were stimulated by plastic-bound IgE (or anti-CD3). It is clear that the Jurkat-derived transfectants, generated by introduction of the scFvCβ, specifically produced IL-2. When we tried to stimulate the transfectants with the SPE-hybridoma cells, we found that soluble IgE secreted by these hybridomas blocked stimulation (exactly like in the 38C.13 system). We therefore fixed the IgE producing hybridoma cells and indeed, as evident in FIG. 17, such cells served as potent stimulators.

Next we checked, using the cytotoxic MD45 T cell hybridoma whether the scFvCβ can arm and trigger cytotoxic cells to eliminate IgE producing cells (known to express IgE on their surface). To mimic the in vivo situation, as target cells we used murine splenic lymphocytes which were induced to produce IgE by culturing them in the presence of lipopolysaccharide (LPS) and IL-4. LPS+IL-4 are known to induce Ig class switch in B cells and specifically trigger IgE and $IgG_1$ formation (50). In the experiments described in FIGS. 18A and 18B, we coincubated MD45 transfectants expressing the anti-IgE scFvCβ with murine lymphocytes, added LPS+IL-4 and monitored both IgE and IgG accumulation into the supernatants of these cultures. As shown in the figure, IgE secretion was completely abrogated in cultures containing the scFvCβ T cells. The effect was very specific as no effect on IgG production could be observed. The suppression of IgE production was most likely due to elimination of IgE producing cells by the redirected scFvCβ-bearing CTL hybridomas. The inability of control 84.1c B cell hybridoma to cause such effect demonstrates that the lack of IgE accumulation in the culture medium is not because of passive absorption of IgE by the 84.1c anti-IgE antibodies. This set of experiments clearly demonstrates that cytotoxic T cells equipped with chimeric scFv-TCR can specifically eliminate their target cells.

Example 5

Endowing Antibody Specificity to the Low Affinity FcγR (FcγRIII) Using Chimeric scFv Joined to the CD16α Chain One of the most attractive candidates for the chimeric receptor approach in natural killer (NK) cells is the low affinity receptor for IgG ((FcγRIIIA) which is composed of the ligand binding CD16α polypeptide associated with the γ chain (51, 52). Triggering of NK cells via FcγRIII (either by anti-CD16 or through immune complexes) includes cytokine production, expression of surface molecules and cytolytic activity (53, 21). The CD16 polypeptide appears as membrane anchored form in polymorphonuclear cells and as transmembrane form ($CD16_{TM}$) in NK (54). The FcγRIII-associated γ chain serves also as part of the FcεRI complex where it appears as homodimer, is very similar to the CD3 ζ chain and can form heterodimers with it in some CTL and NK cells (52, 21, 28, 23-25). Like ζ and η, chimeras between γ and CD4 directed CTL to recognize and kill cells expressing the HIV gp120 (26). Similar chimeric receptors between either the extracellular domain of CD8 (27) or Tac (28) in conjunction with γ, ζ or η have been recently reported in studies mapping the regions of these molecules which take part in the signaling process.

It has been shown in previous examples that the binding domain of a specific antibody in the form of an scFv can serve as the recognition unit of the CD3 ζ (see also 44), TCR Cβ and FcεRI/FcγRIII γ (44). In the present example we report successful experiments in which we constructed and functionally expressed chimeric receptors composed of scFv and anti-TNP and the CD16α polypeptide of the FcγRIII.

In this example, the following materials and methods were used.

A. Design and construction of chimeric scFv-CD16α. For the scFv-CD16α design we have used the scFv of the Sp6 anti-TNP generated before. The entire cytoplasmic and transmembrane and the immediate extracellular region (up to Gly206) of the CD16α (see FIG. 19) were PCR amplified from a human CD16α DNA clone (54), using the primers 18 and 19 of Table I. The truncated CD16 DNA was inserted instead of the γ DNA in the pRSVneoscFvRγ vector previously described.

B. Expression of the chimeric scFv-CD16α.

A. Expression in mast cells. Since the FcγRIII appears as a heterodimer complex consisted of CD16 and γ chains, to check the expression of the chimeric scFvCD16 gene, we transfected it into the rat basophilic leukemia (RBL) cell which is a mast cell expressing functional FcεRI (56). These cells produce excess of γ chain as part of the FcεRI and provide us with convenient function as the receptor-triggered degranulation assay. Following electroporation of the chimeric scFv-CD16α as well as the scFvRγ and scFvRζ genes and selection in G418, RBL clones were obtained which could be surface-stained by the anti-Sp6 idiotypic antibody. FIGS. 20A-20D shows the pattern of FACS analysis of scFvCD16 transfected RBL and FIGS. 21A-21D shows the staining of the scFvRγ and scFvRζ transfectants. Upon the addition of TNP-protein conjugates to the scFvRγ and scFvRζ expressing RBL transfectants, cross-linking of adjacent receptors by the multivalent antigen triggered degranulation as measured by specific release of β-hexoseaminidase to the supernatant (Table II).

TABLE II

Antigen-Specific Degranulation of RBL Cells Transfected With Chimeric scFvRγ And scFvRζ Genes

| Transfected Chain | Stimulatory Antigen | Degranulation % |
|---|---|---|
| — | IgE | 3 |
| — | IgE + DNP – BSA | 22 |
| ScFvRγ | IgE | 3 |
| scFvRγ | IgE + DNP = BSA | 31 |
| scFvRγ | TNP – BSA | 50 |
| scFvRζ | IgE | 3 |
| scFvRζ | IgE + DNP – BSA | 38 |
| scFvRζ | TNP – BSA | 32 |

RBL parental cells and transfectants expressing anti-TNP chimeric scFvRγ or scFvRζ chains were stimulated with SPE anti-DNP IgE with or without its antigen DNP-BSA in order to assess the IgE mediated degranulation of the cells. TNP-BSA on the other hand, served to induce a specific stimulus through the chimeric receptors.
Degranulation was studied by measuring the enzymatic activity of β-hexoseaminidase released to the cell supernatant following degranulation as described before (43).

B. Expression in BW5147 cells. BW5147 is a murine thymoma which does not express surface TCR/CD3 because it does not transcribe either γ or ζ chains. As expected, transfection of the BW5147 cells with chimeric scFvCD16 DNA did not yield any detectable surface receptor, yet intracellular receptor could be detected by immunoblotting of lysates (not shown). When the chimeric scFvCD16 and normal γ DNA were co-electroporated into BW5147 cells, significantly high level of the Sp6 idiotype could be detected on the surface of the transfectants as revealed by immunofluorescence staining and FACS analysis (FIGS. 22A and 22B). The transfectants responded to specific stimulus and produced IL-2 following stimulation with TNP-modified A.20 cells or immobilized TNP-fowl γ-globulin (TNP-FγG) (FIGS. 23 and 24A-24B).

Finally, we checked whether the chimeric scFvIL2R gene (made of the scFv of Sp6 and the β chain of the IL-2 receptor) can be expressed following transfection on the surface of RBL cells. The Sp6-IL-2-R chimeric gene was prepared by joining DNA containing the scFv of Sp6 to a 936 bp DNA segment cloned from PCR amplified DNA (using primers 20 and 23 of Table I) containing the cytoplasmic and transmembrane regions (carboxy 312 amino acids) of the β-chains of the human IL-2 receptor. FIGS. 25A-25D shows the results of immunofluorescence staining of one such RBL transfectant with anti-Sp6 idiotypic antibodies. These results clearly demonstrate that the chimeric scFvIL2R can be expressed as a surface protein.

Example 6

Expression of Chimeric Single-Chain FV Receptors In BW5147 Thymoma Functional Expression In BW5147 Thymoma Cells BW5147 (BW) is a murine thymoma cell line which do not express the TCR or FcγR complexes (due to a defect in the ζ chain transcription (57)), and therefore served as a convenient cell-line to study the expression of the different chimeric scFv receptors. Because BW cells do not produce endogenous ζ or γ chains, it is expected that following transfection, the chimeric receptors will be composed only of homodimers of the exogenous transgenes (in the case of scFvRγ or scFvRζ). Also, it provides a system to study whether the chimeric scFvCD16 can be expressed independently of γ or ζ chains.

The chimeric genes composed of an scFv of Sp6 anti-TNP mAb joined to either one of the ζ, γ or CD16 chains were introduced by electroporation into the BW cells and selected transfectants which grew in the presence of G-418 were analyzed for surface expression of the Sp6 idiotope using the 20.5 anti-Sp idiotypic mAb. In parallel, a group of BW cells was co-transfected with a mixture of scFvCD16+γ chain DNA. The immunofluorescence pattern of staining analysed by FACS is depicted in FIGS. 26A-26D. As can be seen, both BW.Sp6-γ and BW.Sp6-ζ transfectants (which received weither scFvRγ or scFvRζ DNA, respectively) could be specifically stained with anti-Sp6 idiotypic antibody and thus express a moderate level of the chimeric receptor chains on their surface. When studied for CD3 expression, using specific anti-CD3 mAb, we could not observe any surface staining of the scFvRγ or scFvRζ transfectants (not shown), indicating that these chimeric genes are expressed on the cell surface independently of the CD3 complex. None of the transfectants which was electroporated with scFvCD16 alone did express surface receptor (unshown). However, the co-transfection of scFvCD16 and the γ chain DNA yielded transfectants, like the BW.Sp6-CD16 shown in FIGS. 26A-26D, which express the chimeric receptors. These results clearly prove that the CD16 chimeric chain was not sufficient for itself and needed the γ chain for surface expression.

To study whether the chimeric receptors function in the BW cells, we tested the ability of transfectants to undergo stimulation for IL-2 production following stimulation with TNP modified A.20 cells (FIG. 27) or immobilized TNP-FγG (FIG. 28). Although BW cells do not produce any IL-2 following incubation with TNP-labeled antigen, the single-chain receptor expressing transfectants produced IL-2 following stimulation with either cellular or solid-phase antigen.

Taken together these studies demonstrate the appropriate expression of the chimeric chains as functional receptors: they bind ligand with antibody-type specificity on one end and signal for T cell stimulation on the other end. Although we have demonstrated here expression of the chimeric single chain receptors in non-TCR expressing T cells, it is reasonable to expect that natural killer cells, which make use of γ and CD16 in their signaling Fcγ receptor will behave in a similar way.

Example 7

Transduction of Primary T-Cells with a Chimeric Single Chain Fv Receptor Directed Against a Colon Cancer Antigen The specificity of human tumor infiltrating lymphocytes (TIL) has been redirected through modification of these cells with single chain antibody chimeric receptor genes linked to the γ subunit of the Fc receptor (Hwu, P., et al. (1993) *Journal of Experimental Medicine* 178:361-366, herein incorporated by reference). T-cells redirected with single chain antibody chimeric receptor genes (Hwu, P. et al. (1995) *Cancer Research* 55:3369 herein incorporated by reference) have been found to have in vivo antitumor activity. In this example, a chimeric single chain T cell receptor made of an Fv of the GA733 antibody (Herlyn, D., et al. *J. Immunol. Methods* 73:157) and γ chain of the Fc receptor is constructed and introduced into primary, anti-CD3 stimulated peripheral blood lymphocytes (PBL) in order to redirect these T cells against a colon cancer antigen.

Materials and Methods

Construction of GA733 chimeric receptor: Monoclonal antibody (MAb) GA733 (Herlyn, D., et al., (1984) *J. Immunological Methods* 73:157) binds to a 37 kD protein expressed on colorectal carcinoma cells. Total RNA was prepared from a hybridoma cell line expressing MAb GA733 (provided by Dorothee Herlyn, Wistar Institute), followed by reverse transcriptase polymerase chain reactin (RT-PCR), using $V_H$ and $V_L$ primers corresponding to the 5' and 3' consensus amino acid sequences of Ig V regions. A scFv fragment was constructed as described (See FIG. 1), and was then joined to the γ chain of the Fc receptor to make chimeric receptor GA733-γ. The GA733-γ scFv receptor was then cloned into the SAM-EN retroviral vector, 5' to the IRES (internal ribosomal entry site) to make SAM-G7γ-EN. The SAM-EN vector contains a splice acceptor (SA), which was PCR amplified from the 3' terminus of the pol region from wild-type moloney murine leukemia virus (MMLV; Treisman, J. et al. (1995), *Blood* 85:139). The SAM-EN vector contains an LTR promoter from MMLV, as well as a neomycin phosphotransferase gene ($Neo^R$) 3' to the IRES. The SAM-EN and SAM-G7γ-EN retroviral vectors were packaged into the amphotropic packaging cell line PA317 (obtained from ATCC, CRL 9078) as previously described (Hwu, P. et al. (1993) *Journal of Immunology* 150:4104, Hwu, P. et al. (1993) *J. Exp. Med.* 178:361, herein incorporated by reference). Retroviral supernatant was harvested as previously described (Hwu, P. et al. (1993) *J. Exp. Med.* 178:361).

Transduction of PBL

Peripheral blood lymphocytes (PBL) were obtained from normal donors. Mononuclear cells were isolated from buffy coats using a Ficoll-Hypaque gradient, and were grown at $1.0 \times 10^6$ cells per ml. Anti-CD3 (OKT3; Ortho Pharmaceuticals, Raritan, N.J.) was added to a final concentration of 10 ng/ml on the initial day of culture only. PBL were resuspended in retroviral supernatant supplemented with 8 μg/ml polybrene and 600 International Units (IU) of interleukin-2 (IL-2) per ml, and grown in 24-well plates containing 2 ml/well. Every 12 hours, 1 ml of media was removed and replaced with 1 ml of fresh supernatant+polybrene/IL-2 for a total of 6 exposures to the retroviral supernatant. 12 hours after the final exposure to supernatant, ⅔ of the media was removed and replaced with RPMI containing 10% human AB serum and 600 IU IL-2/ml. 24 hours later (day 4 of culture), the PBL were selected in the neomycin analog G418 (Geneticin; Life Technologies, Grand Island, N.Y.) for 5 days. 14 days after culture initiation, PBL were tested for specific cytokine release and lysis.

Cytokine Assay $2 \times 10^5$ PBL were cocultured with $1.0 \times 10^5$ tumor in 250 μl of medium (RPMI/10% human AB/600 IU/ml IL-2) for 24 hours at 37° C. Each sample was performed in duplicate in flat-bottom 96-well plates. Supernatants were then aspirated, centrifuged at 2,000 rpm to remove cells, decanted, and frozen at −70° C. Thawed samples were then tested in an ELISA for human GM-CSF, as previously described (Hwu, P. et al. (1993) *J. Exp. Med.* 178:361). As a positive control, PBL were incubated in wells coated with 2 μg/ml anti-CD3.

$^{51}$Cr Release Cytotoxicity Assay

PBL were evaluated for their ability to lyse specific targets using a standard $^{51}$Cr release assay as described in Hwu, P. et al. (1993) *J. of Immunology* 150:4104, using $^{51}$-Cr-labeled targets.

Results

PBL transduced with the SAM-G7γ-EN receptor against colon cancer produced large amounts of GM-CSF when co-cultured with colon cancer cell lines CY13 and GREM, which express the GA733 antigen. In contrast, less GM-CSF was produced by SAM-G7γ-EN upon coculture with the melanoma cell line 888 MEL or the erythroleukemia cell line K562. Nontransduced PBL and PBL transduced with the SAM-EN control retroviral vector did not produce high amounts of GM-CSF in response to any of the targets. All PBL groups produced high amounts of GM-CSF upon culture with the OKT3 positive control (see Table III below).

TABLE III

GM-CSF Production by PBL

| Stimulator | PBL Responder [GM-CSF] pg/ml/5 × 10⁵ PBL/24 hours | | | |
|---|---|---|---|---|
| | None | Nontransduced | Sam-EN | Sam-G7γ-EN |
| None | 10 | 33 | 26 | 51 |
| OKT3 | 0 | 7560 | 7990 | 8500 |
| K562 | 48 | 197 | 215 | 464 |
| 888 MEL | 12 | 138 | 90 | 174 |
| GREM | 0 | 285 | 132 | 2976 |
| CY13 | 197 | 265 | 248 | 1282 |

SAM-G7γ-EN transduced PBL were also able to lyse colon cancer cells, as seen in Table IV below.
Nontransduced PBL and PBL transduced with the control SAM-EN retroviral vector did not significantly lyse the colon cancer cell line.

TABLE IV

Lysis of Colon Cancer Cell Line CY13 by PBL

| PBL | % Specific Lysis (Effector: Target) | | | |
|---|---|---|---|---|
| | 90:1 | 30:1 | 10:1 | 3.3:1 |
| Nontransduced | 14.3 | 8.4 | 4.8 | 1.3 |
| SAM-EN | 18.9 | 15.0 | 10.4 | 2.4 |
| SAN-G7γ-EN | 52.2 | 38.7 | 22.2 | 10.3 |

These results demonstrate that primary T-cells transduced with a chimeric T-cell receptor against colon cancer can redirect those cells to specifically lyse and secrete cytokine in response to colon cancer cells.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1) Lowder, J. N. et al. Cancer Surv. 4:359-375 (1985).
2) Waldmann, T. A. Science 252:1657-1662 (1991).
3) Jain, R. K. J. Natl. Cancer Inst. 81:64-66 (1989).
4) Mule, J. J. et al. Science 225:1487-1489 (1984).
5) Rosenberg, S. A. et al. Science 233:1318-1321 (1986).
6) Rosenberg, S. A. J. Clin. Oncol. 10:180-199 (1992).
7) Kuwana, Y. et al. Biochem. Biophys. Res. Comm. 149: 960-968 (1987).
8) Gross, G. et al. Transplant. Proc. 21:127-130 (1989).
9) Gross, G. et al. Proc. Natl. Acad. Sci. USA 86:1002410028 (1989).
10) Becker, M. L. B. et al. Cell 58:911-921 (1989).
11) Goverman, J. et al. Cell 60:929-939 (1990).
12) Gross, G. Ph.D. thesis (Weizmann Institute of Science, Rehovot, Israel).
13) Culver, K. et al. Proc. Natl. Acad. Sci. USA 88:31553159 (1988).
14) Kasid, A. et al. Proc. Natl. Acad. Sci. USA 87:473-477 (1990).
15) Adam, M. A. et al. J. Virol. 65:4985-4990 (1991).
16) Huston, J. S. et al. Proc. Natl. Acad. Sci. USA 85:58795884 (1988).
17) Bird, R. E. et al. Science 242:423-426 (1988).
18) Weissman, A. et al. EMBO J. 8:3651-3656 (1989).
19) Bauer, A. et al. Proc. Natl. Acad. Sci. USA 88:3842-3846 (1991).
20) Unkeless, J. C. et al. Annu. Rev. Immunol. 6:251-281 (1988).
21) Ravetch, J. V. and Kinet, J. -P. Annu. Rev. Immunol. 9:457-492 (1991).
22) Wirthmuller, U. et al. J. Exp. Med. 175:1381-1390 (1992).
23) Orloff, D. G. et al. Nature (London) 347:189-191 (1990).
24) Lanier, L. G. et al. J. Immunol. 146:1571-1576 (1991).
25) Vivier, E. et al. J. Immunol. 147:4263-4270 (1991).
26) Romeo, C. and Seed, B. Cell 64:1037-1046 (1991).
27) Irving, B. A. and Weiss, A. Cell 64:891-901 (1991).
28) Letourneur, F. and Klausner, R. D. Proc. Natl. Acad. Sci. USA 88:8905-8909 (1991).
29) Kaufmann, Y. et al. Proc. Natl. Acad. Sci. USA 78:2502-2506 (1981).
30) Rusconi, S. and Kohler, G. Nature (London) 314:330-334(1985).
31) Schoneich, J. et al. J. Immunol. 148:2181-2185 (1992).
32) Eshhar, Z. et al. in Practical Approach to Tumor Immunology, ed. G. Gallagher (IRL, Oxford) in press (1992).
33) Kabat, E. A. et al. Sequences of Proteins of Immunological Importance (Dept. of Health and Human Services, Washington, D.C.) 4th ed. (1987).
34) Colcher, D. et al. J. Nat. Cancer Inst. 82:1191-1197 (1990).
35) Kuster, H. et al. J. Biol. Chem. 265:6448-6452 (1990).
36) Mosmann, T. J. Immunol. Methods 65:55-63 (1983).
37) Kohler, G. and Milstein, C. Eur. J. Immunol. 6:511-519 (1976).
38) Romeo, C. et al. Cell 68:889-897 (1992).
39) Weaver, C. T. and Unanue, E. R. Immunol. Today 11:49 53 (1990).
40) Eshhar, Z. and Gross, G. Br. J. Cancer 62. (Suppl. X), 27-29 (1990).
41) Stancovski, I. et al. Proc. Natl. Acad. Sci. U.S.A. 88:8691-8695 (1991).
42) Bacus, S. et al. Cancer Res. 52:2580-2589 (1992).
43) Schwarzbaum, S. et al. Eur. J. Immunol. 19:1915 (1989).
44) Eshhar, Z et al. Proc. Natl. Acad. Sci. USA 90:720 (1993).
45) Gross, G. and Eshhar, Z. FASEB 6:3370 (1992).

46) Yablonski, D. "Transfection and functional expression of T cell receptor genes". M.Sc. Thesis presented to the Feinberg Graduate School, The Weizmann Institute of Science, Rehovot, Israel (1987).
47) Lin, A. et al. Science 249:677 (1990)
48) Weiss, A. and Stobo, J. J. Exp. Med. 160:1284 (1984).
49) Eshhar, Z. et al. J. Immunol. 124:775 (1980).
50) Snapper, C. et al. J. Immunol. 141:489 (1988).
51) Lanier, L. et al. Nature 342:803 (1989).
52) Anderson, P. M. et al. Proc. Natl. Acad. Sci. 87:2274 (1990).
53) Cassatella, M. A. et al. J. Exp. Med. 169:548 (1989).
54) Ravetch, J. V. and Ferussia, B. J. Exp. Med. 170:481 (1989).
55) Lustgarten, J. and Eshhar, Z., in preparation.
56) Barsumian, E. L. et al. Eur. J. Immunol. 11:317 (1981).
57) Wegener, A. M. et al. Cell 68:83 (1992).

We claim:

1. An adoptive immunotherapeutic method of treating a patient having a cancer bearing tumor-specific antigen with cells having immunological specificity to a selected tumor-specific antigen, comprising administering to said patient cells that have been transformed with a chimeric gene, wherein said cells are peripheral blood lymphocytes, said chimeric gene containing a) a first DNA segment encoding a single-chain Fv (scFv) domain of an antibody directed against the selected tumor-specific antigen and b) a second DNA segment encoding a lymphocyte-activating molecule subunit of a Fc receptor to express the scFv domain and the lymphocyte-activating molecule on the surface of the lymphocytes and to provide said antibody-type specificity.

2. The method according to claim 1, wherein the second DNA segment of chimeric gene encodes at least a portion of transmembrane and cytoplasmic domains of a lymphocyte-activating protein.

3. The method according to claim 2, wherein the second DNA segment of the chimeric gene further encodes an extracellular domain of a lymphocyte-activating protein.

4. The method according to claim 1, wherein the cells are circulating lymphocytes.

5. The method according to claim 4, wherein the cells are primary T cells.

6. The method according to claim 1, wherein the subunit is selected from the group consisting of a gamma chain and a CD16α chain of an Fc receptor.

7. A method of treating a tumor in a patient, wherein said tumor bears immunologically reactive tumor-specific antigens, comprising: transforming cells of the patient with an expression vector wherein said cells are peripheral blood lymphocytes, said expression vector comprising a chimeric gene comprising a first gene segment encoding a single-chain Fv domain (scFv) of an antibody specific to a selected tumor-specific antigen and a second gene segment encoding a molecule selected from the group consisting of a subunit of a Fc receptor and an IL-2 receptor, to express both said scFv domain and said molecule, so that the transformed cells are activated and/or stimulated to proliferate, and exhibit MHC nonrestricted antibody-type specificity when said expressed scFv domain binds to its antigen, and administering the activated cells to the patient, said cells being targeted to the tumor cells, to provide tumor regression.

8. The method according to claim 7, wherein peripheral blood cells of the patient are transformed.

9. The method according to claim 7, wherein the second DNA segment of the chimeric gene encodes at least a portion of the transmembrane and cytoplasmic domains of the molecule.

10. The method according to claim 9, wherein the second DNA segment of the chimeric gene further encodes an extracellular domain of a lymphocyte-activating protein.

11. The method according to claim 7, wherein the cells are circulating lymphocytes.

12. The method according to claim 11, wherein the cells are primary T cells.

13. The method according to claim 7, wherein the subunit is a gamma chain or CD16α chain of an Fc receptor.

14. The method according to claim 7 wherein the tumor-specific antigen is a gastric cancer antigen.

15. The method according to claim 7 wherein the tumor-specific antigen is a breast cancer antigen.

16. The method according to claim 7 wherein the tumor-specific antigen is an ovarian cancer antigen.

17. The method according to claim 1, wherein the chimeric gene is scFvRγ.

18. The method according to claim 1, wherein the chimeric gene is scFvRζ.

19. The method according to claim 1, wherein the tumor-specific antigen is Neu/HER2.

20. The method according to claim 1, wherein the antibody is an anti-HER2 antibody.

21. The method according to claim 20, wherein the anti-HER2 antibody is mAb N29.

22. The method according to claim 1, wherein the Fc receptor is FcγR.

23. The method according to claim 1, wherein the Fc receptor is FcεR.

24. The method according to claim 7, wherein the chimeric gene is scFvRγ.

25. The method according to claim 7, wherein the chimeric gene is scFvRζ.

26. The method according to claim 7, wherein the tumor-specific antigen is Neu/HER2.

27. The method according to claim 7, wherein the antibody is an anti-HER2 antibody.

28. The method according to claim 27, wherein the anti-HER2 antibody is mAb N29.

29. The method according to claim 7, wherein the Fc receptor is FcγR.

30. The method according to claim 7, wherein the Fc receptor is FcεR.

* * * * *

UNITED STATES PATENT AND TRADEMARK OFFICE
CERTIFICATE OF CORRECTION

PATENT NO. : 8,211,422 B2  
APPLICATION NO. : 08/547263  
DATED : July 3, 2012  
INVENTOR(S) : Eshhar et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1277 days.

Signed and Sealed this
Twenty-sixth Day of February, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,211,422 B2  
APPLICATION NO. : 08/547263  
DATED : July 3, 2012  
INVENTOR(S) : Eshhar et al.

Page 1 of 1

It is certified that error appears in the above-identified patent and that said Letters Patent is hereby corrected as shown below:

On the Title Page

Item (63) which reads:

"Continuation-in-part of application No. 08/084,994, filed on Jul. 2, 1993, now Pat. No. 7,741,465"

should read:

--Continuation-in-part of application No. 08/084,994, filed on Jul. 2, 1993, now Pat. No. 7,741,465, which is a Continuation-in-part of application no. PCT/US93/02506, filed March 18, 1993--

Item (30) which reads:

"Mar. 18, 1992  (IL)............101288  
Jan. 31, 1993    (IL)............104570  
Mar. 18, 1993   (WO).........PCT/US93/02506"

should read:

--Mar. 18, 1992  (IL)..................101288  
Jan. 31, 1993    (IL)..................104570--

Signed and Sealed this  
Sixth Day of January, 2015

Michelle K. Lee  
*Deputy Director of the United States Patent and Trademark Office*